US008617879B2

(12) United States Patent  
Yu et al.

(10) Patent No.: US 8,617,879 B2  
(45) Date of Patent: Dec. 31, 2013

(54) APPARATUS FOR CELL OR TISSUE CULTURE

(75) Inventors: Hanry Yu, Singapore (SG); Shufang Zhang, Hangzhou (CN); Hwa Liang Leo, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 56 days.

(21) Appl. No.: 13/260,556

(22) PCT Filed: Mar. 26, 2010

(86) PCT No.: PCT/SG2010/000120  
§ 371 (c)(1),  
(2), (4) Date: Jan. 19, 2012

(87) PCT Pub. No.: WO2010/110754  
PCT Pub. Date: Sep. 30, 2010

(65) Prior Publication Data  
US 2012/0107926 A1    May 3, 2012

(30) Foreign Application Priority Data  
Mar. 26, 2009  (SG) ............................ 200902107-2

(51) Int. Cl.  
C12N 5/00 (2006.01)  
C12M 1/00 (2006.01)  
(52) U.S. Cl.  
USPC ........................................ 435/325; 435/283.1  
(58) Field of Classification Search  
USPC ............................................. 435/325, 283.1  
See application file for complete search history.

(56) References Cited

U.S. PATENT DOCUMENTS

| 7,767,446 B2 * | 8/2010 | Robbins et al. ............ 435/299.2 |
| 8,318,479 B2 * | 11/2012 | Domansky et al. ........ 435/305.2 |
| 2005/0260745 A1 | 11/2005 | Domansky et al. |
| 2008/0085556 A1 | 4/2008 | Graefing et al. |

FOREIGN PATENT DOCUMENTS

| CN | 1218109 A | 6/1999 |
| CN | 1315499 A | 10/2001 |
| CN | 101208422 A | 6/2008 |
| WO | WO 94/28501 A1 | 12/1994 |
| WO | WO 02/44341 A2 | 6/2002 |
| WO | WO 2010/024779 A1 | 3/2010 |

OTHER PUBLICATIONS

Office Action for corresponding Chinese Patent Application No. 201080023013.0, 11 pages, (Dec. 3, 2012).  
PCT International Search Report for PCT Counterpart Application No. PCT/SG2010/000120 containing Communication relating to the Results of the International Search Report, 3 pgs., (May 27, 2010).  
PCT Written Opinion of the International Searching Authority for PCT Counterpart Application No. PCT/SG2010/000120, 5 pgs., (May 27, 2010).  
PCT International Preliminary Report on Patentability (Chapter II of the Patent Cooperation Treaty) for PCT Counterpart Application No. PCT/SG2010/000120, 5 pgs., (Jan. 25, 2011),.  
Esther F. A. Brandon, et al., "An Update on In Vitro Test Methods in Human Hepatic Drug Biotransformation Research: Pros and Cons", Toxicology and Applied Pharmacology, vol. 189, pp. 233-246, (2003).  
J. Landry, et al., "Spheroidal Aggregate Culture of Rat Liver Cells: Histotypic Reorganization, Biomatrix Deposition, and Maintenance of Functional Activities", The Journal of Cell Biology, vol. 101, pp. 914-923, (Sep. 1985).  
Pei Kan, et al., "Perfusion of Medium with Supplemented Growth Factors Changes Metabolic Activities and Cell Morphology of Hepatocyte—Nonparenchymal Cell Coculture", Tissue Engineering, vol. 10, Nos. 9-10, pp. 1297-1307, (2004).  
Jaesung Park, et al., "Microfabricated Grooved Substrates as Platforms for Bioartificial Liver Reactors", Biotechnology and Bioengineering, vol. 90, No. 5, pp. 632-644, (Jun. 5, 2005).  
Jaesung Park, et al., "Radial Flow Hepatocyte Bioreactor Using Stacked Microfabricated Grooved Substrates", Biotechnology and Bioengineering, vol. 99, No. 2, pp. 455-467, (Feb. 1, 2008).

(Continued)

*Primary Examiner* — Karen Cochrane Carlson  
*Assistant Examiner* — Natalie Moss  
(74) *Attorney, Agent, or Firm* — Blakely, Sokoloff, Taylor & Zafman LLP

(57) ABSTRACT

The apparatus for cell or tissue culture comprises a base plate (1), an intermediate face (2) and a top plate (3). The intermediate face (2) is removably sandwiched between the base plate (1) and the top plate (3). The base plate (1) has a circumferential wall (13), a base (14) and a top wall (16). The top wall (16) of the base plate (1) comprises a plurality of recesses (12) arranged in n lines, wherein n is an integer from 1 to about 25. Each line of recesses (12) ranges from a first recess to a last recess. Each recess has a circumferential recess wall (15), which has one recess inlet and one recess outlet (40, 41). The circumferential wall (13) comprises a number of 2 n ports (11). Each port (11) is coupled to a single line of recesses (12). The recesses (12) of each line of recesses are in fluid communication with (i) each other via the recess inlets and a recess outlets (40, 41) and (ii) with a first and a second port (11) of the 2 n ports, such that the first recess of each line of recesses is coupled to a first port and the last recess of each line of recesses is coupled to a second port. The intermediate face (2) has a plurality of recesses (21) arranged in m lines, fitted into the plurality of recesses (12) of the top wall (16) of the base plate (13). m is an integer from 1 to about 25 equal to or smaller than n. The recesses (21) of the intermediate face (2) have water permeability. The top plate (3) is reversibly sealed to the intermediate face (2) and the intermediate face (2) is reversibly sealed to the base plate (1). Thus the recesses (12) of the top wall (16) of the base plate (1) define culture chambers. Each culture chamber has a circumferential wall defined by the recess wall (15) and a removable top, which is defined by a portion of the top plate (3).

15 Claims, 14 Drawing Sheets

(56) References Cited

OTHER PUBLICATIONS

James C. Y. Dunn, et al., "Long-Term In Vitro Function of Adult Hepatocytes in a Collagen Sandwich Configuration", Biotechnology Progress, vol. 7, No. 3, pp. 237-245, (1991).

A. Kern, et al., "Drug Metabolism in Hepatocyte Sandwich Cultures of Rats and Humans", Biochemical Pharmacology, vol. 54, No. 7, pp. 761-772, (1997).

Karen De Smet, et al., "Biotransformation of Trichloroethylene in Collagen Gel Sandwich Cultures of Rat Hepatocytes", Archives of Toxicology, vol. 74, No. 10, pp. 587-592, (2000).

Daniel C. Kemp, et al., "Xenobiotics Inhibit Hepatic Uptake and Biliary Excretion of Taurocholate in Rat Hepatocytes", Toxicological Sciences, vol. 83, No. 2, pp. 207-214, (2005).

Daniel C. Kemp, et al., "Viability Assessment in Sandwich-Cultured Rat Hepatocytes after Xenobiotic Exposure", Toxicology in Vitro, vol. 18, No. 6, pp. 869-877, (2004).

Avi Rotem, et al., "Oxygen Is a Factor Determining In Vitro Tissue Assembly: Effects on Attachment and Spreading of Hepatocytes", Biotechnology and Bioengineering, vol. 43, No. 7, pp. 654-660 (1994).

Randall E. McClelland, et al., "Effects of Enhanced O2 Transport on Hepatocytes Packed within a Bioartifical Liver Device", Tissue Engineering, vol. 10, No. 1, pp. 253-266, (2004).

Takehisa Matsuda, et al., "Phosphorylcholine-Endcapped Oligomer and Block Co-Oligomer and Surface Biological Reactivity", Biomaterials, vol. 24, No. 24, pp. 4517-4527, (2003).

P. Apel, "Track Etching Technique in Membrane Technology", Radiation Measurements, vol. 34, pp. 559-566. (Jun. 2001).

Shufang Zhang, et al., "Microfabricated Silicon Nitride Membranes for Hepatocyle Sandwich Culture", Biomaterials, vol. 29, No. 29, pp. 3993-4002, (2008).

Efrem Curcio, et al., "Mass Transfer and Metabolic Reactions in Hepatocyte Spheroids Cultured in Rotating Wall Gas-Permeable Membrane System", Biomaterials, vol. 28, pp. 5487-5497, (2007).

Jared W. Allen, et al., "In Vitro Zonation and Toxicity in a Hepatocyte Bioreactor", Toxicological Sciences, vol. 84, pp. 110-119, (2005).

\* cited by examiner

Fig. 3B
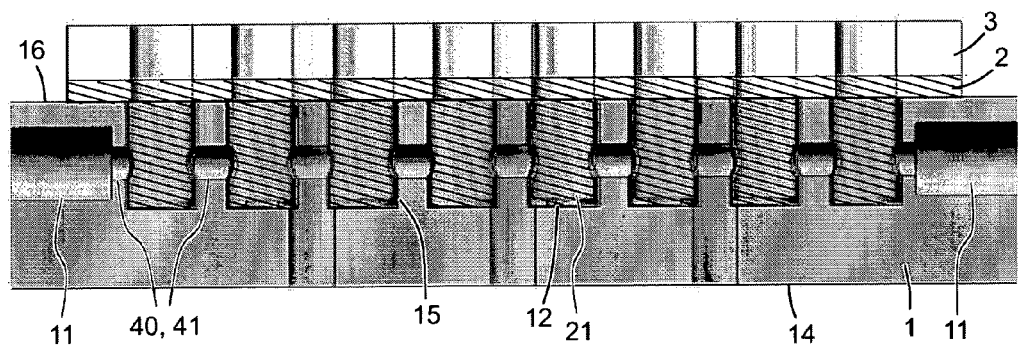
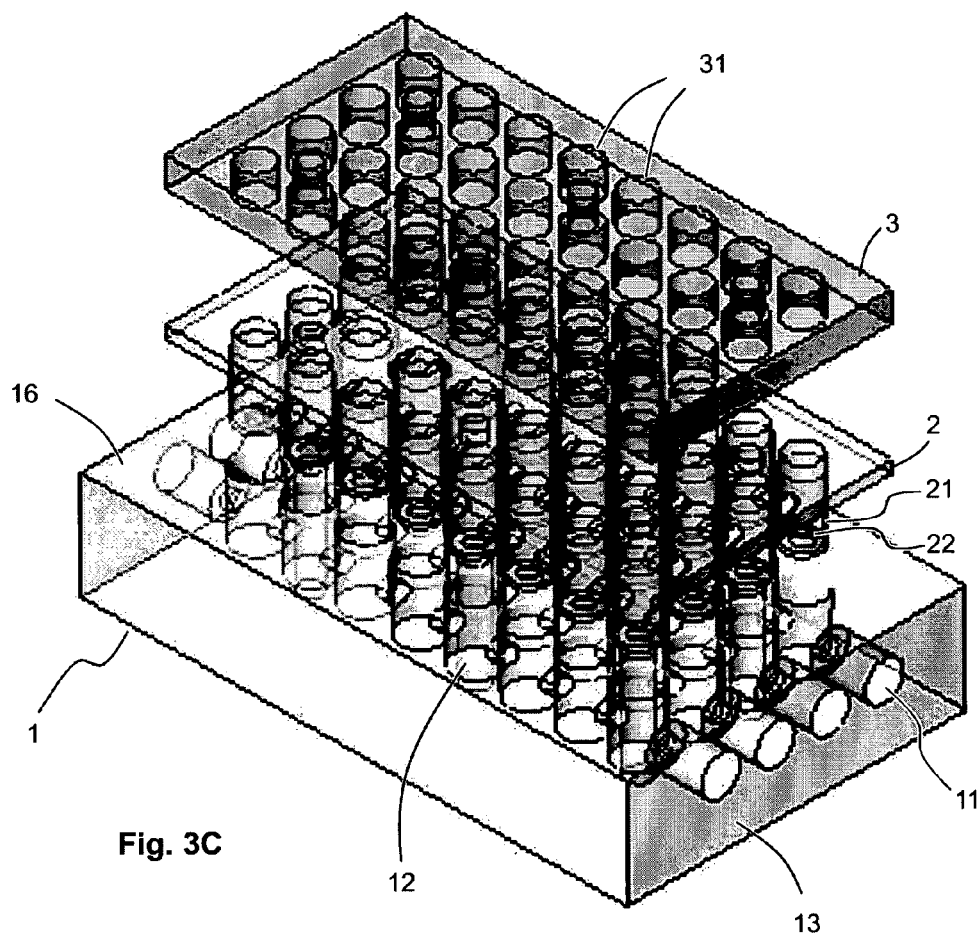
Fig. 3C

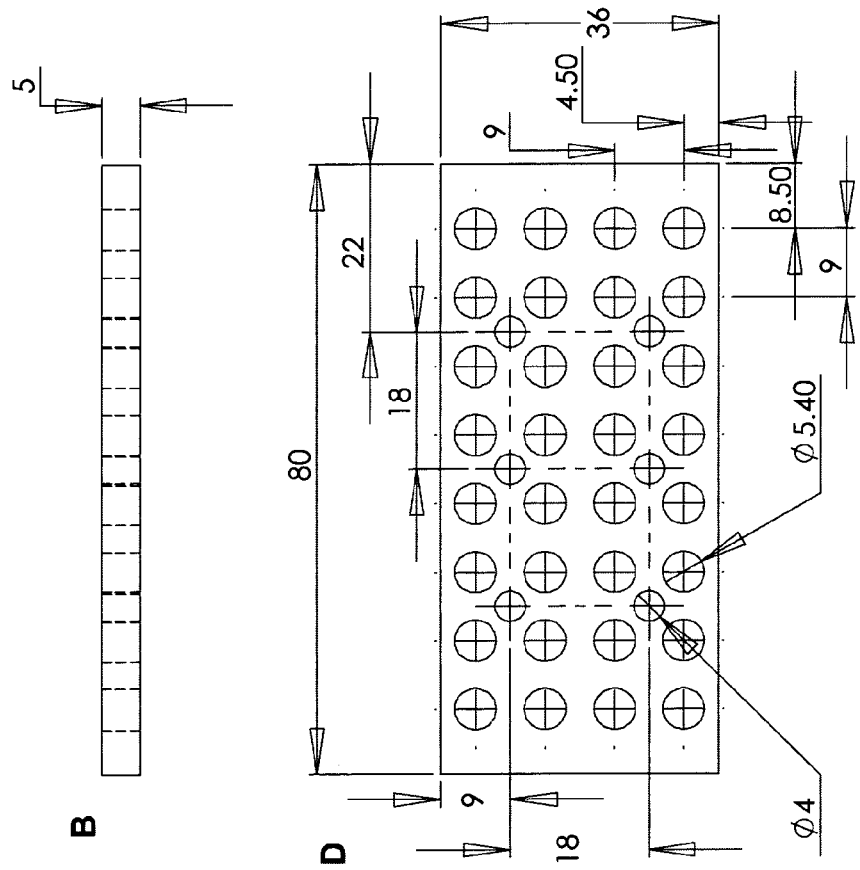
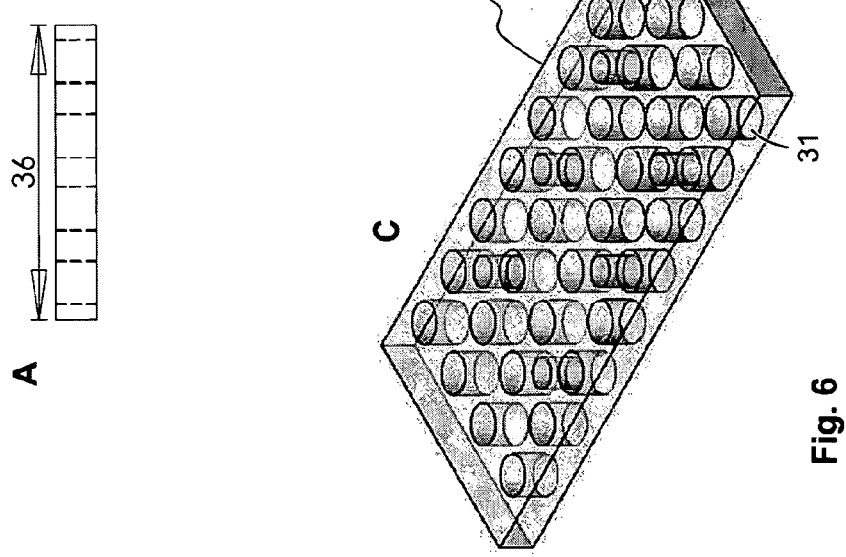
Fig. 6

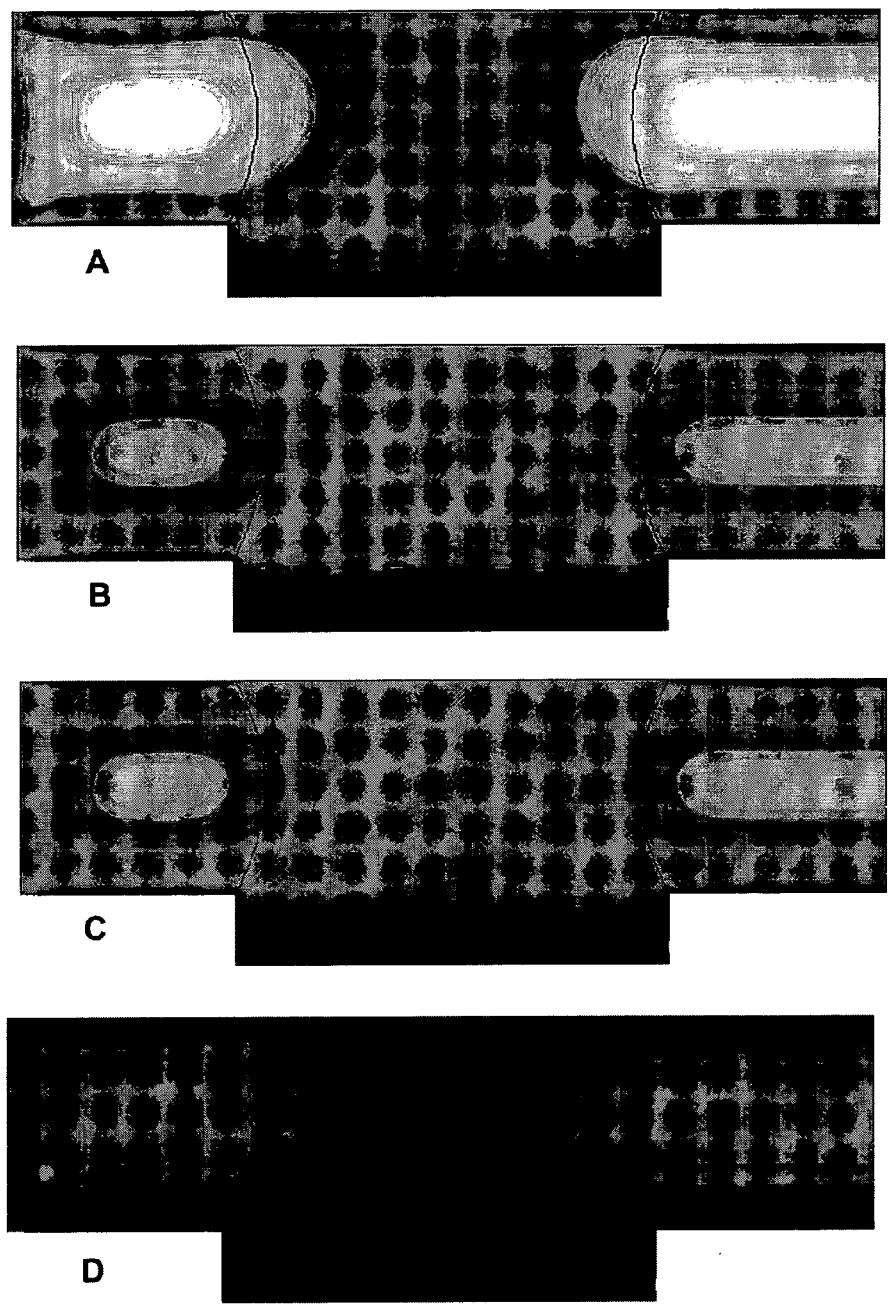
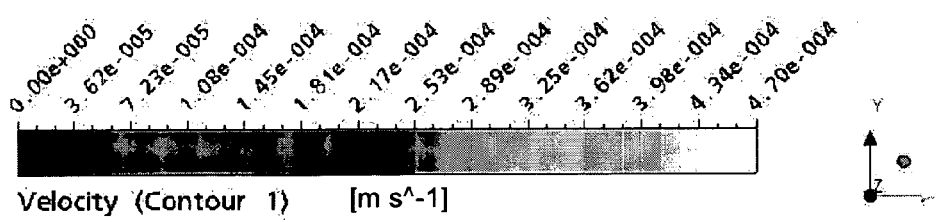
Fig. 9

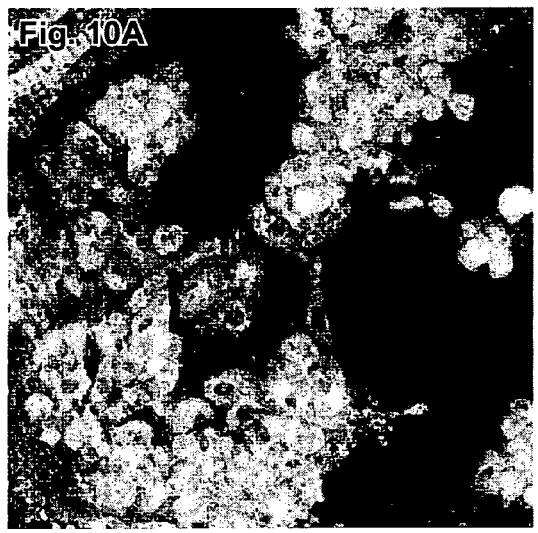
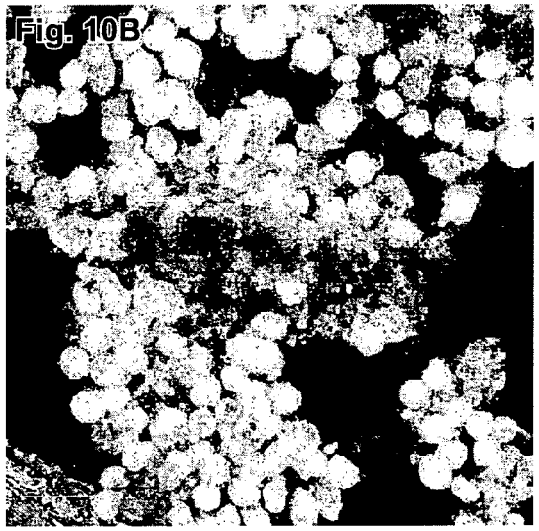
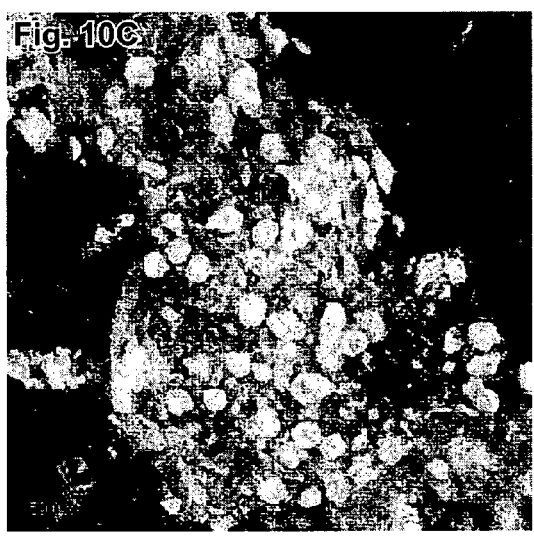
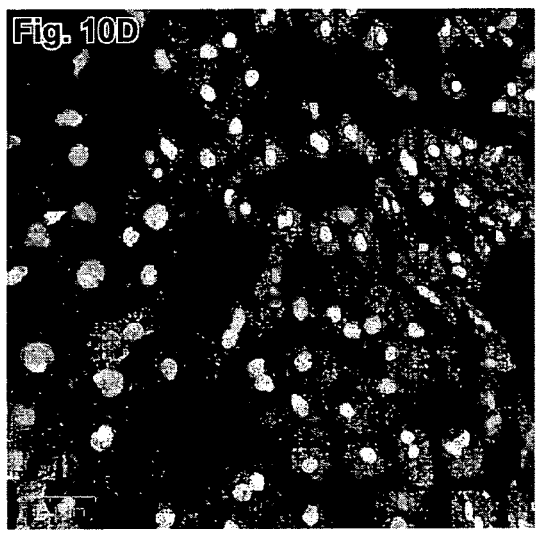

Fig. 10E
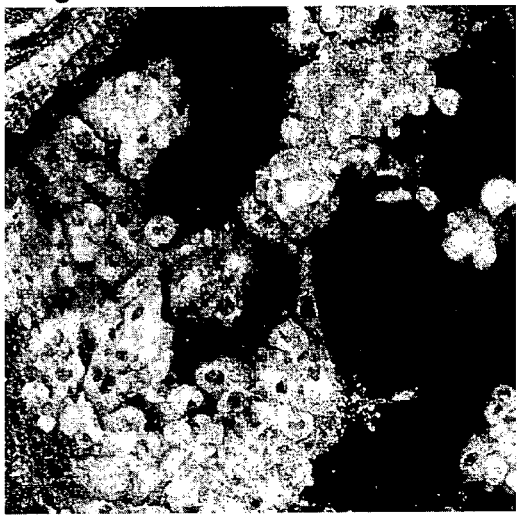
Fig. 10F
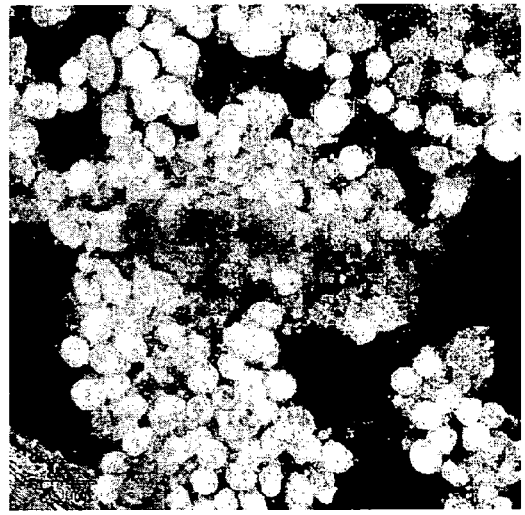
Fig. 10G
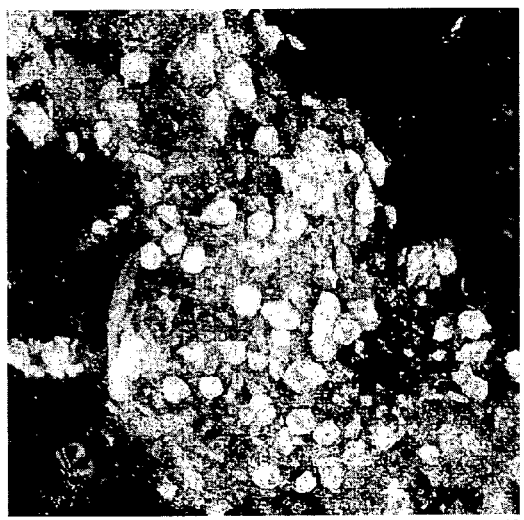
50 µm Fig. 10H
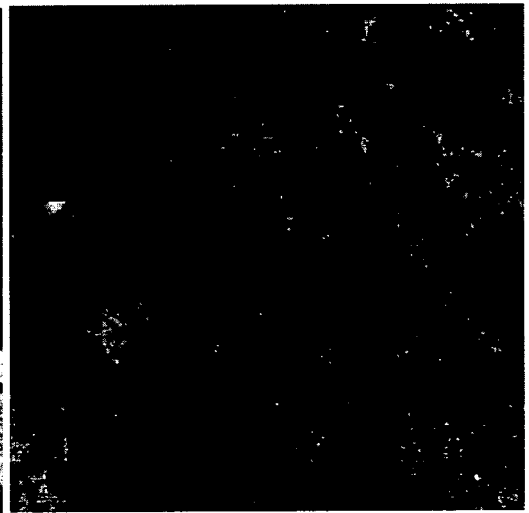

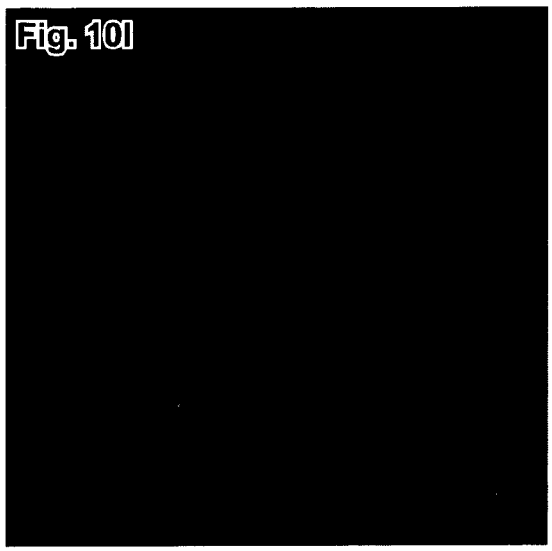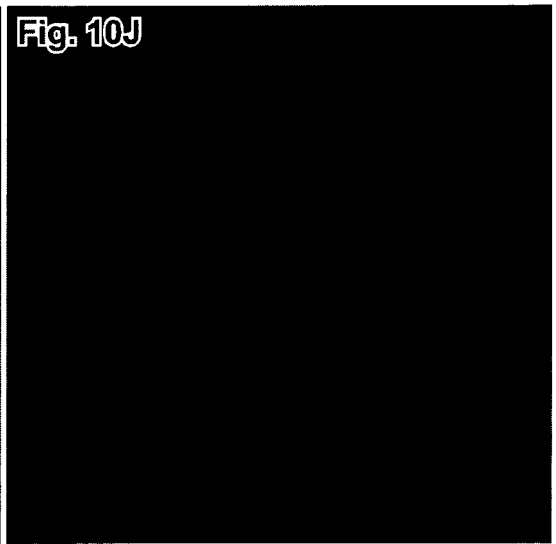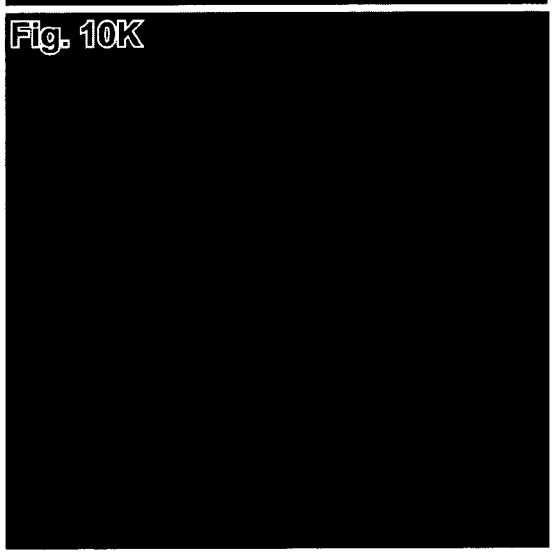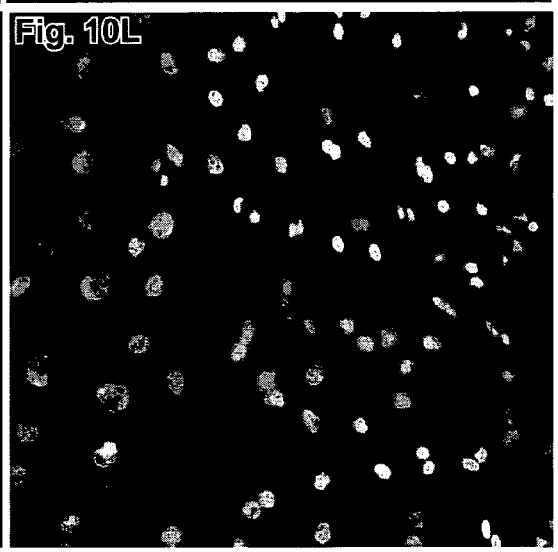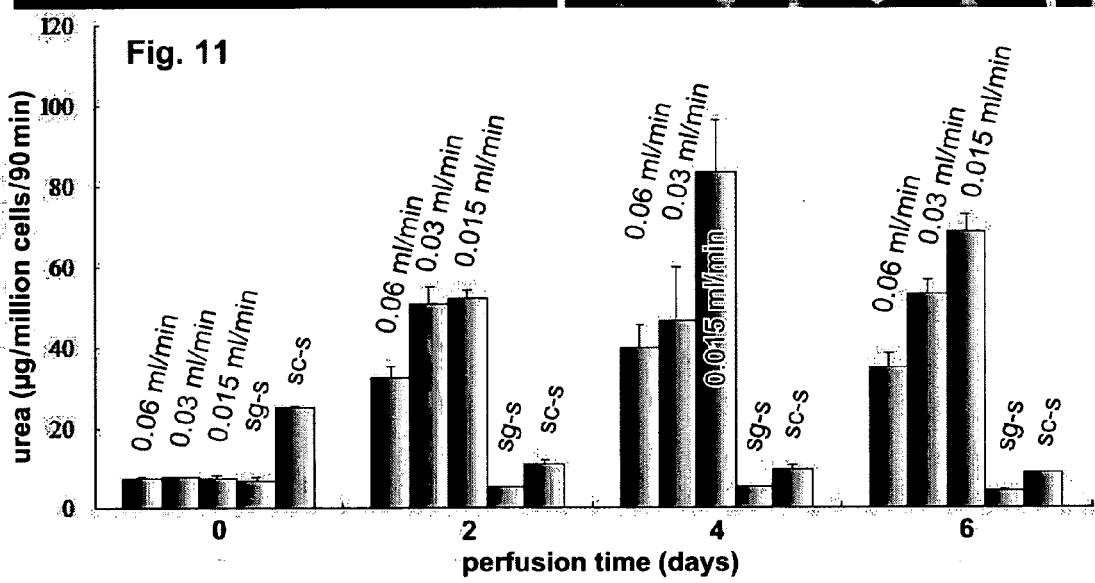

APPARATUS FOR CELL OR TISSUE CULTURE

CROSS REFERENCE TO RELATED APPLICATIONS

This patent application is a U.S. National Phase application under 35 U.S.C.§371 of International Application No. PCT/SG2010/000120, filed Mar. 26,2010, entitled APPARATUS FOR CELL OR TISSUE CULTURE, which makes reference to and claims the benefit of priority of an application for a "96-well perfusion bioreactor for in vitro drug screening" filed on Mar. 26, 2009 with the Intellectual Property Office of Singapore and there duly assigned application No. 200902107-2. The contents of said application filed Mar. 26, 2009 is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates to an apparatus for cell or tissue culture. Provided is also a method of culturing cells based on the use of the apparatus.

BACKGROUND OF THE INVENTION

The development of perfusion bioreactor systems for long term maintenance of functional hepatic culture with a strong predictive power for in vitro drug testing is one of the challenging tasks facing bioengineers (Brandon, E F, Raap, C D, et al., *Toxicol Appl Pharmacol* (2003) 189, 3, 233-246). Primary hepatocytes lose their liver-specific functions upon isolation as a result of the disintegration of in vivo micro-environment characterized by cell-cell interaction, cell-matrix interaction and maximal mass transport. Several methods have been proposed to overcome the loss of cell functionality through the re-establishment of in vivo-like micro-environment for the primary hepatocytes, by using semi-permeable hollow fiber membranes, gel encapsulations, or porous scaffolds. Cell immobilization can be achieved by means of micro-carrier or suspended in collagen gel matrix to form culture of 2D, 3D or spheroids configurations (Landry, J, Bernier, D, et al. J Cell Biol (1985) 101, 3, 914-923; Kan, P, Miyoshi, H, et al. (2004) Tissue Eng 10, 9-10, 1297-1307; Park, J, Berthiaume, F, et al. Biotechnol Bioeng (2005) 90, 5, 632-644; Park, J., Li, Y, et al., Biotechnol Bioeng (2008) 99, 2, 455-467).

Studies have shown that sandwich culture provides microenvironment mimicry of the situation found in vivo. This culturing method provides anchorage for hepatocyte attachment and the establishment of hepatic polarity through the formation of bile canalicular network between contiguous cells, while maintaining the cells' biliary excretion function. Du Y et al reported the re-establishment of hepatic polarity and long-term maintenance of in vitro hepatic functions through the use of bioactive-synthetic materials for their 3D hepatocyte monolayer sandwich culture. The study indicated that the synthetic 3D monolayer culture exhibited a similar process of hepatic polarity formation, better cell-cell interaction and improved differentiated functions over 14-day culture compared to the hepatocytes in collagen sandwich culture. The study highlighted that this technique is ideally suited for liver tissue engineering applications such as drug metabolism/toxicity testing (Dunn, J C, Tompkins, R G, et al. Biotechnol Prog (1991) 7, 3, 237-245; Kern, A, Bader, A, et al. Biochem Pharmacol (1997) 54, 7, 761-772; De Smet, K., Bruning, T, et al. Arch Toxicol (2000) 74, 10, 587-592; Kemp D C, Brouwer, K L, Toxicol In Vitro (2004) 18, 6, 869-877; Kemp, D C, Zamek-Gliszczynski, M J, et al. Toxicol Sci (2005) 83, 2, 207-214)

To maintain cell viability and liver-functions in the primary hepatocytes culture, the application of perfusion bioreactors has been indispensable. Research has demonstrated that perfusion bioreactors enhance mass transport of dissolved oxygen and nutrients to the cell culture, thereby enabling their viability and function (Rotem, A, Toner, M, et al. Biotechnol Bioeng (1994) 43, 7, 654-660; McClelland, R E, Coger, R N, Tissue Eng (2004) 10, 1-2, 253-266). However, many of the existing in vitro perfusion drug testing platforms suffer from the ability to maintain long term cell viability and liver-specific functions. In addition, many of their designs do not conform to the standard cell culture plate dimension, making the transferability of cell cultures to other standard drug testing platforms inconceivably difficult.

There remains therefore a need for a culture platform that addresses the current drawbacks in existing in vitro drug testing bioreactor design.

Accordingly it is an object of the present invention to provide a device or apparatus that overcomes at least some of these drawbacks. This object is solved by providing an apparatus according to claim 1.

SUMMARY OF THE INVENTION

The apparatus of the present invention may be termed a perfusion bioreactor. It may also be used as a module in a cell culture system, which may also be termed a bioreactor system. The apparatus can serve as an in vitro culture platform and integrates known surface modified micro-fabricated sandwich culture into an apparatus architecture that overcomes the above described difficulties in terms of cell viability and tissue specific function. The apparatus further allows the use of standard assay dimensions in terms of multi-well plates and allows even cell transfer between such standard multi-well plate designs and the apparatus of the invention. The apparatus includes a plurality of cell culture chambers, at least some of which include a removable inset that has water permeability and may for instance be a membrane. The insets that have water permeability of a plurality of cell culture chambers are integrated into an intermediate face of the apparatus. This intermediate face is reversibly sealed within the apparatus, so that it can be transferred to another similar apparatus or to a conventional assay platform.

In a first aspect the present invention provides an apparatus for cell or tissue culture. The apparatus includes a base plate, an intermediate face and a top plate. The intermediate face of the apparatus is removably sandwiched between the base plate and the top plate. The base plate has a circumferential wall, a base and a top wall. The top wall of the base plate includes a plurality of recesses arranged in n lines. The number n is an integer from 1 to about 25. Each line of recesses ranges from a first recess to a last recess. Each recess has a circumferential recess wall. This circumferential recess wall of each recess has one recess inlet and one recess outlet. The circumferential wall of the base plate includes a number of 2 n ports. Each port is coupled to a single line of recesses of the n lines, in which the plurality of recesses are arranged. The recesses of each line of recesses are in fluid communication with each other via the recess inlets and a recess outlets. The recesses of each line of recesses are also in fluid communication with a first and a second port of the 2 n ports that are included in the circumferential wall of the base plate. Thus the first recess of each line of recesses is coupled to a first port, and the last recess of each line of recesses is coupled to a second port. The intermediate face of the apparatus has a plurality of recesses. These recesses are arranged in m lines. The number m is an integer from 1 to about 25, and m is equal to or smaller than n (supra). The recesses of the intermediate face of the apparatus are fitted into the plurality of recesses of the top wall of the base plate of the apparatus. The recesses of the intermediate face have water permeability. The top plate of the apparatus is reversibly sealed to the intermediate face of the apparatus. The intermediate face of the apparatus is reversibly sealed to the base plate of the apparatus. Accordingly, the recesses of the top wall of the base plate of the apparatus define culture chambers. Each of these culture chambers has a circumferential wall, which is defined by the respective recess wall of the recesses of the top wall of the base plate of the apparatus. Each culture chamber further has a removable top. This top is defined by a portion of the top plate of the apparatus.

In a second aspect the present invention provides a method of culturing cells. The method includes providing a base plate. The base plate has a circumferential wall, a base and a top wall. The top wall of the base plate includes a plurality of recesses. These recesses are arranged in n lines. The number n is an integer from 1 to about 25. Each line of recesses ranges from a first recess to a last recess. Each recess has a circumferential recess wall. This circumferential recess wall of each recess has one recess inlet and one recess outlet. The circumferential wall of the base plate includes a number of 2 n ports. Each port is coupled to a single line of recesses of the n lines of recesses. The recesses of each line of recesses are in fluid communication with each other via the recess inlets and the recess outlets. The recesses of each line of recesses are further in fluid communication with a first and a second port of the 2 n ports. Accordingly, the first recess of each line of recesses is coupled to a first port and the last recess of each line of recesses is coupled to a second port. The method also includes providing an intermediate face. This intermediate face has a plurality of recesses arranged in m lines. The number m is an integer from 1 to about 25 equal to or smaller than n. The recesses of the intermediate face have water permeability. The plurality of recesses of the intermediate face is capable of fitting into the plurality of recesses of the top wall of the base plate. The method further includes mounting the intermediate face onto the top wall of the base plate. As a result the recesses of the intermediate face fit into recesses of the top wall of the base plate. Further, the method includes seeding cells in the plurality of recesses of the intermediate face. The method also includes providing a top plate. The method includes mounting the top plate onto the intermediate face. As a result the intermediate face is removably sandwiched between the base plate and the top plate. Further, the method includes reversibly sealing the top plate to the intermediate face. The method also includes reversibly sealing the intermediate face to the base plate. As a result the recesses of the top wall of the base plate define culture chambers. Each of these culture chambers has a circumferential wall defined by the recess wall and a removable top. The top of the culture chambers is defined by a portion of the top plate.

BRIEF DESCRIPTION OF THE DRAWINGS

The invention will be better understood with reference to the detailed description when considered in conjunction with the non-limiting examples and the accompanying drawings.

FIG. 1.

FIG. 3 depicts components of an exemplary 96-well perfusion bioreactor and the perfusion route. FIG. 3B is a frontal cross-section of the 96-well bioreactor, 1: base plate, 2 (hatched): intermediate face, 3: top plate, 11: port, 12: recess of base plate, 14: base of base plate, 15: circumferential recess wall, 16: top wall of base plate, 21: recess of intermediate face, 40, 41: recess inlet/outlet of recess of base plate. FIG. 3C is a perspective view of a 96-well bioreactor, 1: base plate, 2: intermediate face, 3: top plate, 11: port, 12: recess of base plate, 13: circumferential wall of base plate, 16: top wall of the base plate, 21: recess of intermediate face, 22: opening of recess of intermediate face, 31: recess of top plate.

FIG. 6 depicts an exemplary top plate (3) in cross-sectional view seen in the direction of a straight line of recesses (A), in cross-sectional view seen sidewise along a straight line of recesses (B), in perspective view (C) (31: recess of top plate) and in top view (D).

FIG. 9 depicts velocity distributions within a 96-well apparatus of the invention at flow rates of 0.1 (A), 0.06 (B), 0.03 (C) and 0.015 ml/min (D).

FIG. 10 depicts cell viability indicated by live (green) and dead (red) staining after 6 days of culture under perfusion at flow rates of 0.015 (A), 0.03 (B), 0.06 (C) and 0.1 ml/min (D). FIGS. 10A-10D are representations of the respective images with both red and green signals (full spectrum). FIGS. 10E-10H are representations depicting only green signals, with saturation of read, yellow, blue, magenta and cyan channels turned to zero.

FIGS. 10I-10L are representations depicting only red signals, with saturation of yellow, green, blue, magenta and cyan channels turned to zero.

FIG. 11 depicts urea production of primary hepatocytes using different methods (as indicated) during a 6-day culture period.

DETAILED DESCRIPTION OF THE INVENTION

Figure 1:
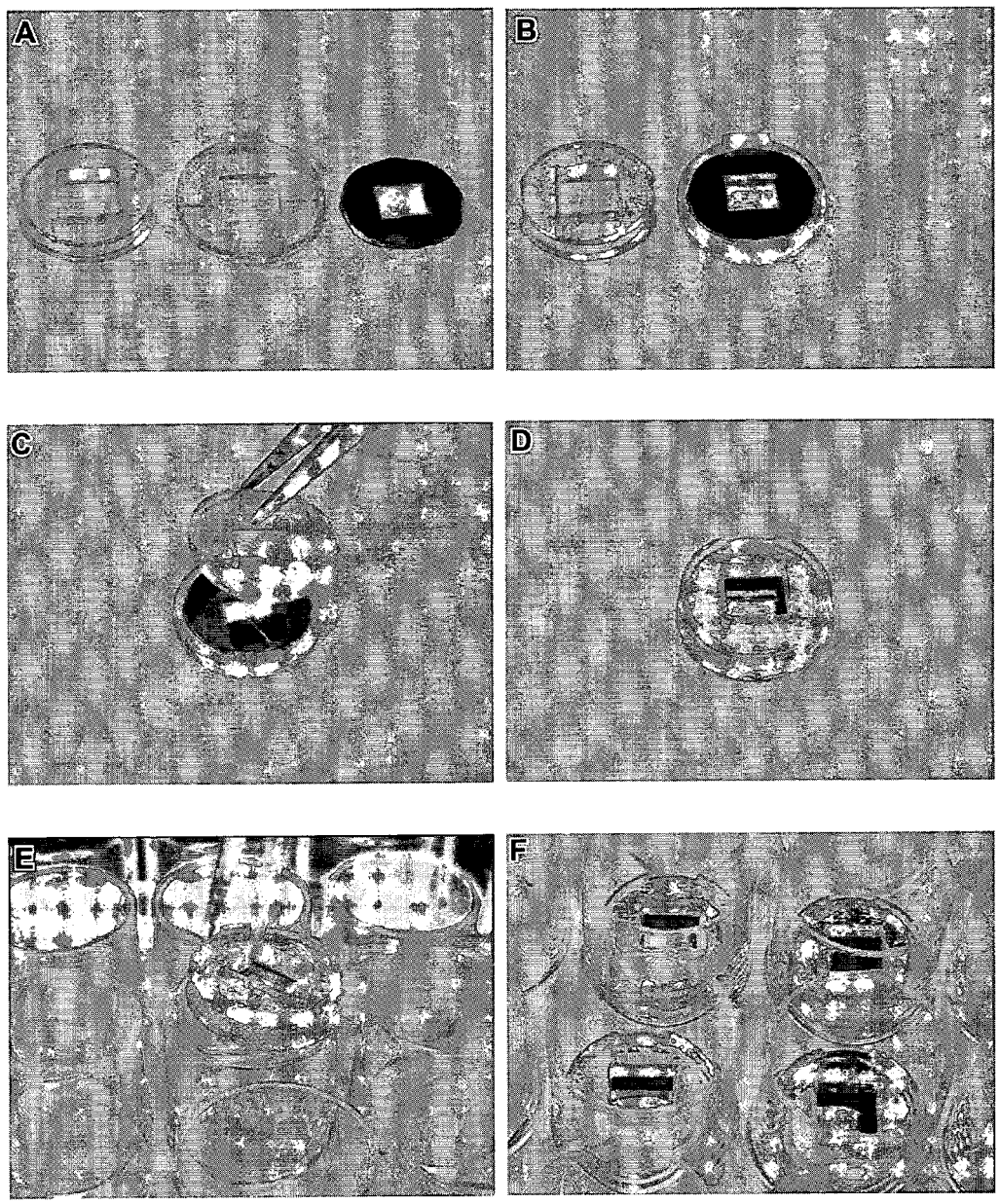
FIG. 1 illustrates a test of assembling a base plate with cells seeded thereon, by overlaying with a galactose-immobilized porous $Si_3N_4$ membrane (A, B) and assembly of a top plate (C) to define a culture chamber (D), which is placed in a suitable container (E, F). Primary rat hepatocytes had been seeded on a galactose-immobilized PET film (base plate) and cultured for 24 hours thereo.

The present invention provides an apparatus for cell or tissue culture. The apparatus includes a base plate, an intermediate face and a top plate. These three elements are removably assembled, typically to provide a water- and air-tight seal. The apparatus may be of any desired dimensions. Typically, the maximal distance spanning the inner cross section of the apparatus, i.e. its maximal width, is selected within the range of about 1 centimeter to about 500 centimeter, about 2 centimeters to about 250 centimeters, about 2 centimeters to about 100 centimeters or about 2 centimeters to about 50 centimeters, such as about 2.5 centimeters to about 25 centimeters, about 4 centimeters to about 25 centimeters, about 2 centimeters to about 15 centimeters, about 4 centimeters to about 15 centimeters, or about 2 centimeters to about 10 centimeters.

The apparatus includes a plurality of culture chambers. These culture chambers may have the same, similar or different geometry and dimensions. Typically the dimensions of the culture chambers of the apparatus are of at least essentially identical size and geometry. The culture chambers are defined by a circumferential wall and a removable top. In some embodiments the culture chambers have a base. The base and the top wall of a culture chamber may be arranged at lest essentially parallel to each other. The circumferential wall and, where present, the base of each culture chamber are defined by a recess in the base plate of the apparatus as further detailed below. The inner cross section of a culture chamber have any desired profile, such as ovoid shape, the shape of a circle, an egg, letters V or U, a triangle, a rectangle, a square, or any polyhedron. In one embodiment where the base and the top wall of a culture chamber are arranged parallel to each other the culture chamber defines an at least essentially cylindrical interior.

The culture chambers may be of any volume. Typically, each of the culture chambers has an interior that provides a volume in the range from about 0.1 ml to about 10 ml, such as about 0.2 ml to about 10 ml or about 0.2 ml to about 5 ml, including about 0.5 ml to about 10 ml, 0.5 ml to about 5 ml or 0.25 ml to about 2.5 ml, such as e.g. 0.35 or 0.5 ml. The interior of a culture chamber means any space or matter that is in direct contact with fluid filled into the culture chamber while any inlets or outlets, e.g. openings, are sealed. It also refers to any space or matter that may be included in space or matter contacting such fluid. As an illustrative example, a circumferential wall of an intermediate face (cf below) that has water permeability is typically removably included in a culture chamber and thus is part of the interior thereof Accordingly the term "inner face", when used in connection with a culture chamber and recess of the base plate, respectively, refers to surface areas that face the interior of the culturing chamber in that they are able to contact fluid filled therein, in particular while any opening is sealed. A culture chamber is then capable of receiving a fluid and/or a sample, e.g. a suspension of cells, blood or plasma, as well as optionally further matter. Hence, in some embodiments a culture chamber is filled with a medium, for instance an aqueous medium for culturing cells, such as one of the well known cell culture media ("growth media") available in the art, e.g. LB medium; a monosaccharide containing liquid—possibly including e.g. Hank's Salts; Eagle's minimal essential medium (including e.g. Dulbecco's Modified Eagle Medium); RPMI (Roswell Park Memorial Institute) medium; HyClone medium; Ham's tissue culture medium; Chee's medium; YM Broth; or Murashige and Skoog medium, to name a few, or blood. In other embodiments it may be desired to fill a culture chamber with such medium in order to culture cells or to detoxify the medium by means of cells present in the culture chamber.

The culture chambers may be designed to be capable of accommodating any desired fluid (cf. also below). The fluid may be of any properties, whether polar or non-polar. Typically the fluid is an aqueous liquid such a cell culture medium, blood or plasma. Through an inlet in the circumferential wall the fluid may be disposed into, or enter, the culture chamber. Through an outlet in the circumferential wall the fluid may exit the culture chamber.

Within the interior of a culture chamber there may be provided further elements such as one or more sensors such as nano sensors, e.g. for detecting temperature or oxygen levels, or one or more oxygen support elements. Oxygen support elements may for example be designed to include capillaries that are in fluid contact with an external oxygen supply. Such elements are in direct contact with fluid filled into the culture chamber and are thus included in the interior of the culture chamber. Further matter in communication with such elements, such as tubing or wiring, is however typically not in direct contact with fluid filled into a culture chamber and thus not part of the interior of a culture chamber.

The circumferential wall, where present the base, and the removable top wall of the culture chambers as such thus act to prevent any communication between fluid filled into the chamber and the surrounding environment. Generally the base, the circumferential wall and where present the removable top wall thus prevent any fluidic communication between the interior of the chamber and the surrounding environment. Elements such a sensor or an oxygen support element are designed to prevent fluid communication with the interior of the chamber by means of a membrane or one or more walls. Where an oxygen support element has a membrane via which a fluid such as a gas is permitted to contact fluid filled into the chamber and to dissolve therein, any direct communication between the respective fluids is prevented by the barrier provided by the membrane. The term "fluid communication" is accordingly understood not to include diffusion or osmosis across a barrier. Any inlets or outlets that such elements may have, for instance in order to allow supply with a fluid, are accordingly neither in fluid communication with fluid filled into the chamber and thus not part of the interior of the chamber.

As mentioned above, the circumferential wall of a culture chamber has, however, an inlet and an outlet. Via the inlet and the outlet—and generally only via the inlet and the outlet, since no additional inlets or outlets are generally present—the interior of a culture chamber is in fluid communication with the environment. Independent from one another the inlet and the outlet may consist of or may include any means. Each of them may for instance be an opening, a channel or a valve. A respective opening, as well as the profile of a respective channel, may be of any size and shape. Examples include, but are not limited to, the shape of a circle, rectangular or square shape or the shape of a triangel. In some embodiments the inlet and or the outlet of the housing of the apparatus may be entirely sealable.

As already indicated above, the culture chambers of the apparatus can be assembled and disassembled by positioning and reversibly sealing the base plate and the top plate of the apparatus. Additionally, an intermediate face is included upon assembly, which is positioned between the base plate and the top plate of the apparatus.

The base plate of the apparatus has a circumferential wall, a base and a top wall. The base plate may include any desired material. Typically, it is solid and able to remain intact during the entire culturing process to be performed in the apparatus. As a few illustrative examples, the base plate, or a portion or element thereof, may include glass, polypropylene (PP) or polytetrafluoroethylene (PFTE, Teflon). In some embodiments the base plate may include or consist of an elastomer, such as a silicon polymer, e.g. polydimethylsiloxane, polypropylmethylsiloxane, polytrifluoropropylmethylsiloxane, or polyphenylmethylsiloxane. The use of an elastomer may be desired to facilitate reversibly sealing the base plate to the intermediate face. The same may apply mutatis mutandis to the top plate of the apparatus.

In some embodiments at least a portion of the base plate, e.g. the circumferential wall, the base and/or the top wall, is of matter that allows light to enter into the interior of the apparatus, including for instance the culture chambers that are included in the apparatus. The term "light" is understood to include electromagnetic radiation of any wavelength, including a distinct wavelength, a set of distinct wavelengths or any region of the electromagnetic spectrum. Two examples of a region of the electromagnetic spectrum are visible light, corresponding to a wavelength range of about 400 to about 700 nanometers, and ultraviolet light, corresponding to a wavelength range of about 30 to about 400 nanometers. In some embodiments at least a portion of the circumferential wall, the base and/or the top wall is of matter that allows light to emerge from the interior of the apparatus, including the culture chambers. A respective wall (including base) portion that allows light to emerge may be identical to, overlapping with or different from a wall portion (including a base) that allows light to enter the culture chamber. A wall portion may for instance be transparent or translucent. Examples of suitable material for a wall portion that allows light to pass include, but are not limited to, glass, quartz and plastic material. Suitable plastic materials for the construction of a respective wall portion include, but are not limited to, polymethyl-methacrylates (e.g. polymethyl-methacrylate (PMMA) or carbazole based methacrylates and dimethacrylates), polystyrene, polycarbonate, and polycyclic olefins. A further illustrative example of a material that is additionally suitable for the generation of a wall portion that allows light to pass only to a certain extent is fluoro-ethylen-propylen (FEP).

Both the base and the top wall of the base plate may be of any inner and outer geometry and include any desired material. In some embodiments the base and/or the top wall may for instance be curved, round, straight or flat. The base and/or the top wall may in some embodiments a flat plate of for example rectangular, square, triangular, ovoid or circular profile. The base and/or the top wall may be arced, such as concave or convex, undulated, or include a dent, a nook or any other geometrical element. In typical embodiments both the base and the top wall are solid and able to remain intact during the entire culturing process to be performed therein. Any one of the base, the circumferential wall and the top wall of the base plate of the apparatus may in some embodiments be a part of another, typically larger, wall or base, respectively. In some embodiments the base, the top wall and the circumferential wall of the base plate include one or more identical material(s). In one embodiment the base, the top wall and the circumferential wall of the base plate are made of the same material(s). The base and the top wall may be arranged at any desired orientation with regard to each other. In some embodiments one or both of the base and the top wall of the base plate are arranged at least essentially perpendicular to the circumferential wall thereof. In one embodiment the base and the top wall of the base plate are arranged at least essentially parallel to each other.

The circumferential wall of the base plate may be the surface of a solid base plate or a wall of a certain thickness. In the latter case it may be of any thickness/strength, as long as it capable of remaining at least essentially intact during the culture of cells in the apparatus when assembled. In some embodiments the geometry of the outer shape of an apparatus of the invention may to a large extent be determined by the base plate and thereby largely by the circumferential wall thereof.

The base of the base plate typically provides a contact surface with matter of the ambience onto which the apparatus is placed, e.g. a surface of table. The base of the base plate may accordingly be designed to have a geometry and surface characteristics that is well suited for the apparatus to be placed onto a desired surface. In some embodiments the base of the base plate is thus a plain surface.

The terms "horizontal", "vertical", "below", "above", "lower", "upper", "top" and "on top" as used herein, refer to a position, where the apparatus of the present invention is oriented in such a way that the plurality of culture chambers of the apparatus are oriented in a plane that is at least essentially perpendicular to the direction of gravitational force of the earth. In this orientation to top plate of the apparatus is arranged in a position relative to the interior of the culture chambers that is at least essentially opposite the direction of gravitational force of the earth. In this regard the culture chambers are arranged in lines (see also below). Such a line of culture chambers is generally arranged in a plane within the apparatus, which is oriented at least largely (if not at least substantially) perpendicular to the direction of the gravitational force of the earth. Typically this plane defined by the arrangement of the culture plates is at least roughly parallel to the ground. In this orientation the inlets and outlets of the culture chambers are arranged, relatively to the culture plates, in the plane of the culture plates and point in a direction that is at least largely perpendicular to the direction in which the gravitational force of the earth is acting. In this orientation the circumferential wall of the base plate of the apparatus typically extends at least roughly about the direction of gravitational force of the earth.

The top wall of the base plate of the apparatus includes a plurality of recesses. Each of these recesses may have its own individual topography and geometry. The size and dimensions of the recesses of the plurality of recesses may be individually selected. Each of the plurality of recesses has a circumferential recess wall. The inner face(s) of the recesses may be defined by this circumferential wall. In some embodiments one or more, including each, recess has a circumferential recess wall and a recess base. If the apparatus is arranged in a position with the base plate oriented in the direction about perpendicular to gravity, recesses of the top plate have a certain maximal width in this plane perpendicular to the direction of gravity. An inner cross section of a recess in this plane may have any desired profile, such as semi-ovoid shape, the shape of a semicircle, letters V or U, a triangle, a rectangle, a square, or any polyhedron.

In some embodiments the top wall of the base plate, which can be taken to define an upper surface thereof, is at least essentially planar. Such a planar top wall of the base plate may further be arranged within the assembled apparatus in such an orientation that it defines a plane perpendicular to the direction of gravity when the apparatus is positioned on the ground, a table etc., and in operation. This plane may be arranged at least essentially parallel to the surface of the earth when the apparatus is in operation. The above mentioned maximal width of the recesses in a direction about perpendicular to gravity is in such embodiments a maximal width in the plane of the base wall of the top plate of the apparatus.

The circumferential recess wall and, where present, the recess base may possess any surface characteristics, as long as they allow the storage of a medium, in particular a liquid. The surface characteristics as well as the material of the circumferential recess wall and, where present, the recess base may be selected to match the needs of cells that are to be cultured in the apparatus. In some embodiments any surface or surface portion of a recess may be rendered hydrophilic or hydrophobic. If desired, different portions of a recess may provide different surface characteristics.

A treatment of a recess, another part of the base plate or any other part of the apparatus that achieves an alteration of surface characteristics may be any treatment that leads to an alteration of the respective surface characteristics that lasts long enough for a subsequent contact to fluid, such as a cell culture medium, or to cells, to be affected. Typically, this treatment does not affect the composition of fluid contacting the respective surface area. In some embodiments the treatment does not affect the composition of any fluid that contacts the respective surface area.

Treatment that may be carried out to alter surface characteristics may comprise various means, such as mechanical, thermal, electrical or chemical means. A method that is commonly used in the art is a treatment with chemicals having different levels of affinity for the fluid sample. As an example, the surface of plastic materials can be rendered hydrophilic via treatment with dilute hydrochloric acid or dilute nitric acid. As another example, a polydimethylsiloxane (PDMS) surface can be rendered hydrophilic by an oxidation with oxygen or air plasma. Alternatively, the surface properties of any hydrophobic surface can be rendered more hydrophilic by coating with a hydrophilic polymer or by treatment with surfactants. Examples of a chemical surface treatment include, but are not limited to exposure to hexamethyldisilazane, trimethylchlorosilane, dimethyldichlorosilane, propyltrichlorosilane, tetraethoxysilane, glycidoxypropyltrimethoxy silane, 3-aminopropyltriethoxysilane, epoxy-cyclohexyl)ethyltrimethoxysilane, 3-(2,3-epoxy propoxyl) propyltrimethoxysilane, poly-dimethylsiloxane (PDMS), γ-(3,4-epoxycyclohexyl)ethyltrimethoxysilane, poly(methyl meth-acrylate), a polymethacrylate co-polymer, urethane, polyurethane, fluoropolyacrylate, poly-(methoxy polyethylene glycol methacrylate), poly(dimethyl acrylamide), poly [N-(2-hydroxy-propyl)methacrylamide] (PHPMA), α-phosphorylcholine-o-(N,N-diethyldithiocarbamyl)-undecyl oligoDMAAm-oligo-STblock co-oligomer (see Matsuda, T et al., Biomaterials (2003), 24, 24, 4517-4527), poly(3,4-epoxy-1-butene), 3,4-epoxy-cyclohexylmethylmethacrylate, 2,2-bis[4-(2,3-epoxy propoxy) phenyl]propane, 3,4-epoxy-cyclohexylmethylacrylate, (3',4'-epoxycyclohexylmethyl)-3,4-epoxycyclohexyl carboxylate, di-(3,4-epoxycyclohexylmethyl)adipate, bisphenol A (2,2-bis-(p-(2,3-epoxy propoxy)phenyl) propane) or 2,3-epoxy-1-propanol.

Via the inlet and the outlet a number of culture chambers, and thus the corresponding number of recesses in the top wall of the base plate of the apparatus, are in fluid communication with each other. Culture chambers may for example be coupled by means of a conduit, for example connecting two adjacent culture chambers. The conduit may couple, e.g. connect, the outlet of a first culture chamber with the outlet of a second culture chamber. A respective conduit, e.g. a below-surface-channel, may in some embodiments of a maximal width across its cross section that is selected in the range from about 0.2 to about 6 mm, such as about 0.5 to about 6 mm, about 1 to about 5 mm, about 2 to about 5 mm or about 1 to about 4 mm.

Culture chambers, and thus recesses in the top wall of the base plate, that are in fluid communication with each other are arranged in n lines. The integer n indicates the number of such lines that are included in the top wall of the base plate of the apparatus. The integer n is generally selected in the range from 1 to about 30, such as from 1 to about 25, from 1 to about 20, from 1 to about 15, from 1 to about 12, from 1 to about 9 or from 1 to about 5, such as e.g. 1, 2, 3, 4, 5, 6, 7, 8, 9, 10, 11, 12, 13, 14, 15 or 16 lines. Each line of recesses in the top wall of the base plate, and thus each line of culture chambers, ranges from a first recess/culture chamber to a last recess/culture chamber. Between the first and the last recess/culture chamber a number of additional culture chambers/recesses may be arranged and coupled in series. Each of these additional culture chambers is thus positioned between two culture chambers/recesses and connected to adjacent culture chambers/recesses via the recess inlet and recess outlet in its circumferential wall. The number of culture chambers between the first and the last recess may be selected in the range from 0 to about 100, such as 0 to about 50, 0 to about 40, 0 to about 30, 0 to about 25, 0 to about 20, 0 to about 15, 0 to about 10 or 0 to about 5. In embodiments where n is larger than 1, i.e. where a plurality of lines of recesses is arranged in the top wall of the base plate, the recesses of these lines may be arranged in any suitable array. As also explained further below, such an array may correspond to a standard multi well format, such as a 6-, a 12-, a 24-, a 48-, a 96-, a 384- or a 1536 well format. As indicated above, the culture chambers/recesses of a line of culture chambers/recesses is arranged in a common plane. In some embodiments this plane is at least substantially parallel to the plane defined by the base of the base plate of the apparatus.

The first and the last recess/culture plate of each line of culture chambers/recesses is coupled to, including connected to, a port, which is included in the circumferential wall of the base plate of the apparatus. Generally each such port is connected to only one culture chamber/recess and thus coupled to only one line of culture chambers/recesses. Each line of culture chambers/recesses is thus coupled to two respective ports, one port being coupled, including connected, to the first recess/culture chamber of the line, one port being coupled, including connected, to the last recess/culture chamber of the line. A respective port may for example be connected to the first or respectively last recess/culture chamber via a conduit. Accordingly, the circumferential wall of the base plate of the apparatus includes a total of 2 n ports.

As indicated above, typically a culture chamber/recess of the apparatus includes an inset that has water permeability. The inset can be taken to act as a sieve. Water permeability may be provided by an aperture such as an opening. Such an opening may have maximal width selected in the range from about 0.1 to about 6 mm, such as from about 0.2 to about 5 mm, e.g. of for example about 5 mm, about 4 mm, about 3 mm, about 2 mm, about 1 mm or about 0.5 mm., A respective opening may be selected to have dimensions that are small enough to prevent cells of choice from passing through the same. A respective opening may also be arranged in a position where this opening of the inset faces a portion of the circumferential wall of the recess of the top wall of the base plate that is free of an inlet or outlet. Accordingly, the inlet and outlet of the recess of the top wall of the base plate and the opening of the inset are arranged in non-overlapping positions. In such an embodiment the opening of the inset and the inlet and/or outlet of the recess in the base plate cannot define a continuous passage (i.e. a channel). Whether selected cells can be prevented from passing from the opening of the inset through the inlet and/or outlet of the respective recess in the base plate is then typically determined by the maximal distance between the circumferential wall of the inset and the circumferential wall of the recess in the base plate. If these circumferential walls are close-fitting, most cell types are typically prevented from exiting from the inset. In some embodiments the inset is water permeable in that is of a water permeable material. In some embodiments the inset is both water permeable and includes an aperture.

This inset allows, to a pre-selectable degree, fluid to pass. In operation the apparatus may provide a continuous flow of fluid through the n lines of recesses/culture chambers. This flow of fluid can accordingly be allowed to pass the fluid-permeable inset and thereby perfuse the culture chamber. The mass transport provided by the fluid flow may allow for instance metabolites, nutrients and dissolved oxygen to diffuse into and out of a culture chamber. The inset may also serve as a scaffold or adherence substrate for anchorage-dependent cells. The inset may for example be porous. It may have a predefined pore size and a predefined inter-pore distance selected for improved mass transport. The inset may for instance be defined by a track-etch membrane, which may include a polymer such as polyethylene terephthalate (PET), polyvinylidene fluoride (PVDF), polypropylene (PP), a polyimide, CR-39 or polycarbonate (PC). The shape of pores in such a membrane may be freely selected. The shape of pores can be controlled upon their formation to be for instance cylindrical, conical, funnel-like, or cigar-like. An overview on the technique of track-etching has for example been given by Apel (Radiation Measurements (2001) 34, 559-566). The inset may in some embodiments be of gas-permeable material such as poly(1-trimethylsilyl-1-propyne) or an aromatic polyacetylene, e.g. poly[1-phenyl-2[p-(triphenylsilyl)phenyl]-acetylene] or 2-[p-(triisopropylsilyl)phenyl]acetylene].

The inset may have the shape of a basket or a hemisphere. The inset is fitted into the culture chamber/recess and may have a shape and dimensions that match the shape and dimensions of the circumferential wall and, where present, the base of the culture chamber/recess. The respective inset is in itself a recess of the intermediate face of the apparatus of the invention. Accordingly, this recess of the intermediate face may have an outer shape and outer dimensions that correspond to the inner shape and the inner dimensions of the corresponding recesses of the top wall of the base plate into which the recess of the intermediate face is fitted. The intermediate face may have a maximal width in the direction of the distance between the base plate and the top plate of the apparatus, i.e. a thickness, that provides sufficient mechanical stability that allows the intermediate face to remain at least essentially intact during operation of the apparatus. The thickness is typically selected to be small enough to at least essentially not affect, not interfere with, or at least not prevent perfusion operation of the apparatus. The exact thickness of the intermediate face will thus usually depend on the other dimensions and parameters of the apparatus, and on the material of the intermediate face. As an illustrative example, the thickness may be selected in the range from about 0.1 to about 2 mm, such as from about 0.2 to about 1 mm, from about 0.3 to about 0.8 mm, from about 0.1 to about 0.8 mm or from about 0.3 to about 0.6 mm, e.g. 0.4 or 0.5 mm.

Where a water-permeable material is used for the recesses of the intermediate face the skilled artisan will take the action of capillary forces into consideration when designing the intermediate face. If the entire intermediate face is of water-permeable material, culture medium may leak from the recesses of the intermediate face via the residual intermediate face. It may thus be desired in some embodiments where larger portions, including the entirety of the intermediate face are of water-permeable material to provide one or more seals or gaskets to stop the action of capillary forces.

The recess of the intermediate face may also be selected to have a smaller depth, i.e. a smaller dimension in the direction of gravity (cf. above) than the recess in the base plate into which it is inserted. Likewise, the recess of the intermediate face may also be selected to have a smaller width, i.e. a smaller dimension in the direction perpendicular to the direction of gravity (cf. above) than the recess in the base plate into which it is inserted. In such embodiments a void may remain between the circumferential wall and/or, where present, between the base of the culture chamber/recess and the inset defined by the recess of the intermediate face. As explained below, cells are cultured by seeding them on the recesses of the intermediate face. Accordingly, the architecture of the apparatus of the invention incorporates a configurable well depth that allows the fine tuning of fluid-induced shear stress on the cell surface. By selecting a desired depth and width of recesses of the intermediate face, relative to the depth and width of recesses of the top wall of the base plate, the effective well depth and well diameter in which cells are cultured can be adjusted. Such an adjustment allows manipulating and fine-tuning the fluid-induced shear stress on the cell surface of cells cultured in the culture chambers. For such adjustments, as well as comparisons in this regard, the same base plate with different intermediate faces or the same intermediate face with different base plates can be used and/or evaluated.

The intermediate face of the apparatus has a plurality of recesses that are fitted into the plurality of recesses of the top wall of the base plate. In one embodiment the number of recesses in the intermediate face of the apparatus is identical to the number of recesses in the top wall of the base plate. In this embodiment each recess of the top wall of the base plate includes a recess of the intermediate face, fitted therein. As indicated above, the dimensions of the recesses of the intermediate face are about identical to or smaller than the dimensions of the recesses in the top wall of the base plate. In some embodiments the number of recesses in the intermediate face of the apparatus is smaller than the number of recesses in the top wall of the base plate. In such an embodiment only a number of recesses of the top wall of the base plate that is smaller than the total number of such recess of the top wall of the base plate includes a recesses of the intermediate face. The recesses of the intermediate face are arranged in m lines, with m being an integer equal to or smaller than n (supra). Hence, depending on the value of n, m may be selected in the range from 1 to about 30, such as from 1 to about 25, from 1 to about 20, from 1 to about 15, from 1 to about 12, from 1 to about 9 or from 1 to about 5, such as e.g. 1, 2, 3, 4, 5, 6, 7, 8, 9, 10, 11, 12, 13, 14, 15 or 16 lines.

A line, including each line of recesses in the top wall of the base plate may have a number of recesses selected in the range from 1 to about 200. As explained above, typically each line of recesses has a first recess coupled to a first port in the circumferential wall of the base plate and a last recess coupled to a second port in this wall. Where the first and the last recess are different recesses, the number of recesses in each line of recesses is 2 or higher. In some embodiments the number of recesses in a line of recesses may accordingly be selected in the range from 2 to about 200. In some embodiments each line of recesses in the top wall of the base plate has an independently selected number of o recesses, with o being an integer. The individual integers may for instance be distinguished as o, o', o" etc. This integer o may be 1, 2 or higher. As an example, o may be independently selected in the range from 1 to about 200, including, 2 to about 200, 2 to about 150, 1 to about 150, 2 to about 120, 2 to about 100, 1 to about 100, 2 to about 80, 2 to about 60, 2 to about 50, 1 to about 50, 2 to about 40, 1 to about 40, 2 to about 30, 1 to about 30, 2 to about 25, 1 to about 25, 2 to about 20, 1 to about 20, 2 to about 12 or 1 to about 12. In one embodiment the integers o of all lines of recesses in the top wall of the base plate are identical.

The number of recesses in each line of recess of the intermediate face may be identical to or smaller than the number of recesses in the corresponding line of recesses in the top wall of the base plate, into which the line of recesses is fitted. In some embodiments the number of recesses in at least one line of the m lines of recesses of the intermediate face is identical to the number of recesses in at least one line of the n lines of recesses of the top wall of the base plate. In one embodiment the number of recesses in at least one line of recesses of the intermediate face is identical to the number of recesses in the corresponding line of recesses of the top wall of the base plate into which the line of recesses of the intermediate face is fitted. In this embodiment all the culture chambers defined by this at least one line of recesses of the top wall of the base plate have an inset, which is defined by a corresponding recess of the intermediate face. A line, including each line of recesses in the intermediate face may have a number of recesses selected in the range from 1 to about 200. In some embodiments each line of recesses in the intermediate face has an independently selected number of p recesses, with p being an integer. The individual integers may for instance be distinguished asp, p', p" etc. This integer p may be 1, 2, 3 or higher. As an example, o may be independently selected in the range from 1 to about 200, including, 2 to about 200, 2 to about 150, 1 to about 150, 2 to about 120, 2 to about 100, 1 to about 100, 2 to about 80, 2 to about 60, 2 to about 50, 1 to about 50, 2 to about 40, 1 to about 40, 2 to about 30, 1 to about 30, 2 to about 25, 1 to about 25, 2 to about 20, 1 to about 20, 2 to about 12 or 1 to about 12. In one embodiment the integers p of all lines of recesses in the intermediate face are identical. In one embodiment the integers p of all lines of recesses in the intermediate face are identical to the integers o of all lines of recesses in the top wall of the base plate, into which they are fitted.

While the recesses of the intermediate face of the apparatus are generally of water-and gas-permeable material, the residual portion on the intermediate face, i.e. the portion that is not a recess and does not include a recess, may be of any desired material. In some embodiments this residual portion is likewise of water- and gas-permeable material, which is in one embodiment the same material as the material of the recesses of the intermediate face. In other embodiments the residual portion is of a solid material that is, at least essentially, not water- and gas-permeable. Typically any portion of the intermediate face is nevertheless of a material that is able to remain intact during the entire culturing process to be performed in the apparatus.

In one embodiment all recesses of the intermediate face are of the same material. In some of these embodiments the entire intermediate face is of the same material. As an illustrative example the intermediate face, or at least the recesses thereof, may include or be of silicon nitride ($Si_3N_4$), for instance in the form of an ultra-thin micro-fabricated porous silicon nitride membrane as described previously (Zhang, al. 2008, supra). The surface of the intermediate face, or at least the recesses thereof, may further be modified by a selected treatment. As an illustrative example, a crresponding micro-fabricated silicon nitride ($Si_3N_4$) membrane may have been surface modified with galactose ligands, for instance in order to provide enhanced cell attachment.

The intermediate face of the apparatus may have any desired shape and dimensions, as long as the shape and dimensions allow a tight assembly in the form of a sandwich, where the intermediate face is positioned between the top face of the base plate and the top plate of the apparatus. The intermediate face may for example have a shape and dimensions that match the shape and dimensions of the top wall of the base plate. In some embodiments the intermediate face is of smaller dimensions in the plane defined by the line of culture chambers than the base plate. The intermediate face may in some embodiments have a shape and dimensions that are adapted to, e.g. match, the shape and dimensions of the top wall of the base plate in such a way that all the recesses of the intermediate face fit into a recesses of the top wall of the base plate. In embodiments where at least one line of recesses of the intermediate face fits into at least one line of recesses of the top wall of the base plate that has an identical number of recesses the intermediate face may have a shape and dimensions that are adapted to, e.g. match, the shape and dimensions of the top wall of the base plate in such a way that it allows the recesses of the intermediate face fitting into the at least one line of recesses of the top wall of the base plate to be inserted therein.

The portion or portions of the intermediate face that differ(s) from the recess(es) therein may be of the same material as the respective recesses or of different material. In embodiments where a plurality of recesses is included in the intermediate face, the portion or portions of the intermediate face that differs from recesses may include a range between individual recesses of the intermediate face. In some embodiments the portion or portions of the intermediate face that differ(s) from the recess(es) is at least essentially planar. Such a planar intermediate face may further be arranged within the assembled apparatus in such an orientation that it defines a plane perpendicular to the direction of gravity when the apparatus is positioned on the ground, a table etc., and in operation. This plane may be arranged at least essentially parallel to the surface of the earth when the apparatus is in operation.

The material of the recesses of the intermediate face is usually selected to allow accommodation of cells within the recesses of the base plate. The recesses of the intermediate face are permeable for water, nutrients and gases, so that cells kept in these recesses can be exposed to a continuous supply of nutrients and oxygen once the apparatus is in use and fluid such as plasma or cell culture medium flows through the lines of recesses in the base plate of the apparatus. On the other hand the material of the recesses of the intermediate face allows maintaining the cells therein. As an illustrative example, where the material of the recesses of the intermediate face is porous, the pore size is usually selected to be small enough to prevent cells from passively passing through the intermediate face. The material of the recesses of the intermediate face and/or any treatment, including e.g. coating, thereof may also be selected to prevent cells of a selected cell type from actively migrating through the intermediate face. This allows any desired design of the inlets and outlets of the recesses of the base plate, since there is no risk that cells may get washed out of the corresponding cell culture chamber via inlet or outlet.

The design of the apparatus of the invention with recesses of a removable intermediate face allows the intermediate face to be provided as a reusable or as a disposable component of the apparatus. This design also allows transferring cells from the apparatus of the invention to any other platform of corresponding well architecture, such as a commercially available analysis or testing workstations, e.g. a liquid handling robot or an automated robotic liquid handling/analysis system. A respective platform may be based on the architecture of microplates with 96, 384, 1536, or 3456 wells, as conventionally employed in automated screening systems, for instance in HTS and uHTS. Thus an apparatus of the invention can be used to culture cells and to provide the cultured cells in a format ready for testing, without having to physically transfer cell cultures individually. This prevents disrupting the cultures and compromising their viability. The intermediate face is well suited for serial-cum-parallel flow perfusion in the apparatus of the invention. Where the recesses/culture chambers for instance match the positions of a conventional 96-well plate, the intermediate face can be transferred to a regular 96-well plate on the robotic system for further evaluation. Any washing or incubation steps can be carried out using the respective robotic system, so that no additional time, which could compromise cell viability, is required before analysis can be carried out. Hence, the intermediate face can be taken to provide a link between the apparatus of the invention and a commercial system.

As explained above, a top plate is reversibly sealed to the intermediate face of the apparatus. For this purpose a sealing fluid such as a gel or a liquid may for example have been cured or otherwise processed, e.g. in a temperature driven reaction. A sealing material may include a polymer that is derived from a photosensitive and/or heat-sensitive polymer precursor. The seal between intermediate face and top plate, as well as the seal between base plate and intermediate face is reversible in that it can be released. The seal may also be achieved by a sufficiently accurate match of the dimensions and surface geometry of the intermediate face and the top plate. The same applies accordingly to a match between intermediate face and base plate. As indicated above, in some embodiments the seal may be achieved by an appropriate selection of a flexible material to be included in the intermediate face and/or in the top plate. In some embodiments additional matter in form of a sealing means may be arranged within the housing such as a gasket, e.g. an O-ring. Such sealing means may be of any suitable rigid or semi-rigid material. In some embodiments a sealing material may be applied to provide a desired tight seal, e.g. a sealing fluid in form of e.g. a gel or a liquid, which may harden to form or to maintain a tight seal. As an illustrative example a sealing material may include a polymer that is derived from a photosensitive and/or heat-sensitive polymer precursor. Thus, the sealing material may be formed from a respective precursor after positioning it at the contact face between the top plate and the intermediate face, by polymerisation. A corresponding sealing process may be of reversible or irreversible nature, as long as the seal itself can be released. As an example, without oxidative treatment PDMS forms a non-covalent reversible seal with smooth surfaces. A respective sealing may in some embodiments be performed by a glue. Any glue that is compatible with the desired use of the apparatus in culturing cells may be used.

The top plate may be of any inner and outer geometry and include any desired material. It may for instance be curved, round, straight or flat. It may be arced, such as concave or convex, undulated, or include a dent, a nook or any other geometrical element. In typical embodiments at least the lower surface of the top plate, which contacts the intermediate face of the apparatus is at least essentially straight, including plain and may be taken to define a straight wall. Generally the top plate is of at least essentially water-impermeable material. In some embodiments the top plate is of at least essentially water- and gas-impermeable material. The top plate is of a size and dimensions that it contacts the intermediate face to an extent that all recesses of the intermediate face are covered and closed by the top plate. Generally the top plate is of a size and dimensions that it is arranged above the base plate to an extent that all recesses of the base plate are covered and closed by the top plate. Accordingly, generally all circumferential walls of recesses of the base plate define circumferential walls of culture chambers, since all recesses of the base plate are generally included in culture chambers.

The top plate generally has a top wall, which may be taken to be an upper surface, facing the ambience and a base wall, which can be taken to be a lower surface, facing the intermediate face. In some embodiments the (typically removable) top plate of the apparatus has one or more recesses. Such a recess/recesses may be arranged in the base wall (lower surface) of the top plate. Where the apparatus is assembled such a recess typically faces the intermediate face. Such a recess may have a circumferential wall. A respective recess may also have a base. In some embodiments such a recess may span about half, about two thirds, about % or more of the maximal width of the top plate, typically in the direction about opposite to gravity when the apparatus is arranged in a position with the base plate oriented in the direction of gravity (cf. above). In some embodiments a respective base of a recess in the top plate may be taken to be defined by the top wall of the top plate. In such embodiments the base of the recess in the top plate may be of gas-permeable material.

In some embodiments these recesses are arranged at positions that correspond to the positions of recesses in the intermediate face, fitted into recesses of the base plate (supra). In some embodiments all recesses included in the top plate are arranged at positions that correspond to positions of recesses in the base plate. In some embodiments the number of recesses in the top plate is identical to the number of recesses in the intermediate face. In one embodiment the number of recesses in the top plate, the number of recesses in the intermediate face and the number of recesses in the base plate are identical. If the apparatus is arranged in a position with the top plate oriented in a direction about perpendicular to gravity, recesses of the top plate have a certain maximal width in this plane perpendicular to the direction of gravity. This maximal width of the recesses may in some embodiments be about identical to or smaller than the maximal width of the recesses in the base plate in this plane. The circumferential wall of the corresponding recess in the base plate, the circumferential wall of the corresponding recess in the top plate, as well as—if present—the base of the recess in the base plate and the base of the recess in the top plate can then be taken to define a culture chamber as explained above. The part of this culture chamber defined by the recess in the top plate of the apparatus can be taken to define a removable top of a culture chamber. Within a respective culture chamber a recess of the intermediate face of the apparatus may be fitted in such a way that it is fitted into the recess of the top wall of the base plate. Thereby the recess of the intermediate face defines an inset within the culture chamber (supra).

In some embodiments the base wall (lower surface) of the top plate is at least essentially planar. Such a planar base wall of the top plate may further be arranged within the assembled apparatus in such an orientation that it defines a plane perpendicular to the direction of gravity when the apparatus is positioned on the ground, a table etc., and in operation. This plane may be arranged at least essentially parallel to the surface of the earth when the apparatus is in operation. The above mentioned maximal width of the recesses in a direction about perpendicular to gravity is in such embodiments a maximal width in the plane of the base wall of the top plate of the apparatus. In one embodiment both the top wall of the base plate and the base wall of the top plate are at least essentially planar and define planes that are arranged in parallel. In this embodiment the intermediate face is planar and switched between the top wall of the base plate and the base wall of the top plate. Accordingly, the intermediate face is in this embodiment likewise at least essentially planar and defines a plane that is arranged parallel to the planes of the base wall of the top plate and the top wall of the base plate.

As already explained above, for cell or tissue culture cells are seeded or tissue is placed in the plurality of recesses of the intermediate face. These of recesses of the intermediate face can be taken to define insets of the culture chambers of the apparatus as explained above. Seeding cells or placing tissue into these insets is typically carried out before the apparatus is entirely assembled by sealing the top plate onto the intermediate face. Cells may for example be seeded by dispensing, which may also be carried out using a dispensing or a pipetting robot. Where a tissue sample is placed into a recess, the dimensions of the tissue sample may be selected to at least essentially match the dimensions of the recess into which it is to be placed.

Accordingly, a method of culturing cells and/or tissue includes providing a base plate as defined above. An intermediate face as defined above is provided and mounted onto the top wall of the base plate. By mounting the intermediate face onto the top wall of the base plate the recesses of the intermediate face fit into recesses of the top wall of the base plate. Cell/tissue culture medium may be provided and positioned into the wells defined by the recesses seeding cells in the plurality of recesses of the intermediate face. Any desired cell or tissue type may be seeded/positioned in the wells. Cells may for instance be cells of a cell line or cells isolated from the ambience. The cells may have been obtained from an organism. In some embodiments the cells have been isolated from an organism. In some embodiments the cells have been directly isolated from an organism while in other embodiments the cells have been isolated from an organism and subsequently been grown in culture before including them into an apparatus of the invention. In some embodiments the cells are animal cells, e.g. cells of a mammalian species, including a rodent species, an amphibian, e.g. of the subclass Lissamphibia that includes e.g. frogs, toads, salamanders or newts, an invertebrate species, or of a plant. Examples of mammals include, but are not limited to, a rat, a mouse, a rabbit, a guinea pig, a squirrel, a hamster, a hedgehog, a platypus, an American pika, an armadillo, a dog, a lemur, a goat, a pig, an opossum, a horse, an elephant, a bat, a woodchuck, an orang-utan, a rhesus monkey, a woolly monkey, a macaque, a chimpanzee, a tamarin (saguinus oedipus), a marmoset or a human. The cells may for instance be cells of a tissue, such as an organ or a portion thereof. Examples of a respective organ include, without being limited thereto, adrenal tissue, bone, bladder, brain, cartilage, colon, eye, heart, kidney, liver, lung, muscle, nerve, ovary, pancreas, prostate, skin, small intestine, spleen, stomach, testicular, thymus, tumour, vascular or uterus tissue, or connective tissue. In some embodiments the cells include hepatocytes. Cells that may be seeded include anchorage-dependent cells and cells that are grown in suspension. In some embodiments a suitable anchorage substrate for anchorage-dependent cells is deposited in a portion of the interior of the culture chambers. In order to maintain a sufficient contact of the cells to the flow of cell culture medium it may be advantageous to test in advance which amount of anchorage substrate is tolerated in a selected recess of the intermediate face without significantly affecting nutrient/oxygen supply or without affecting cell viability beyond an acceptable level. Generally the anchorage substrate is deposited first before cells are seeded. As mentioned above, anchorage-dependent cells may also be provided with ligands such as galactose ligands to support cell attachment. Such ligands may be immobilized directly on the intermediate face, thereby redundantising the use of any anchorage substrate (cf. Zhang et al., 2008, supra). In some embodiments the same cell type is seeded into all wells into which cells are seeded. In some embodiments different cells are seeded into different wells.

To avoid loss of the cell culture medium the ports in the circumferential wall of the base plate may be closed. Cells may be seeded or tissue positioned into any desired number of the recesses of the intermediate face, including all recesses of the intermediate face. A top plate as defined above may be provided and mounted onto the intermediate face. Hence, the intermediate face is removably sandwiched between the base plate and the top plate as explained above. The top plate may be reversibly sealed to the intermediate face as explained above. Likewise the intermediate face may be reversibly sealed to the base plate. Thereby the apparatus as defined above may be assembled. The recesses of the top wall of the base plate and a portion of the top plate define culture chambers as explained above. Each culture chamber has a circumferential wall that is defined by the recess wall as well as a removable top, which is defined by a portion of the top plate.

The ports of the circumferential wall of the base plate may be couple to a fluid reservoir. The ports may also be couple to a pump such as a peristaltic pump, for example in order to maintain the cells and/or tissue by providing a continuous flow of nutrients and oxygen.

A respective apparatus may further include further devices that provide desired functions such as maintaining an appropriate ambience in terms of e.g. temperature, atmosphere composition and humidity. Accordingly, sensors, including nano- or micro-sensors, for monitoring relevant data such as pH, temperature, oxygen level or the level of a selected metabolite may be included in the apparatus. The apparatus may also be included in a cell culture system that may also include a device for mechanical blood filtration, including blood purification by e.g. sorption, hemofiltration and/or diafiltration. As an illustrative example, the system may include a dialysis module for continuous hemofiltration.

Once the apparatus has been assembled the flow of a medium may be allowed through the apparatus. The medium is allowed to enter the apparatus via the ports of the circumferential wall of the base plate (supra). As explained above, ports of the bottom plate of the apparatus may be fluidly coupled to a fluid source such as a medium source. Since the recesses in the top wall of the base plate are arranged in line and coupled to each other via inlets and outlets they are coupled in series. Accordingly a serial flow with medium flowing from one recess/culture chamber to a subsequent recess/culture is allowed using the apparatus of the invention. In embodiments where n is large than 1 (see above), several lines of recesses/culture chambers are arranged in the top wall of the base plate in parallel. Such a design allows a parallel flow of medium in recesses/culture chambers of different lines of recesses/culture chambers. Each line of recesses in the top wall of the base plate and thus of culture chambers has a first recess coupled to a first port and a last recess coupled to a second port (supra). If medium is allowed to enter the first port, it will accordingly flow through the line of culture chambers and exit the apparatus via the second port. Therefore the flow of a medium through the n lines of culture chambers defined by the recesses that are arranged in the base plate can be allowed and controlled individually for each of the n lines. Accordingly, the flow rate, including the flow direction, in each line of recesses/culture chambers may be controlled individually and independently from the flow rate in other line(s) of recesses/culture chambers that may be arranged in the apparatus. Hence, continuous in vitro perfusion can be provided for cells cultured within the recesses of the intermediate face of an apparatus of the invention.

In order that the invention may be readily understood and put into practical effect, particular embodiments will now be described by way of the following non-limiting examples. It is understood that modification of detail may be made without departing from the scope of the invention.

Exemplary Embodiments of the Invention

Stability of Hepatocyte Morphology in Microfabricated Porous $SI_3N_4$ Membrane Based Sandwich ($SI_3N_4$—SC)

Figure 2:
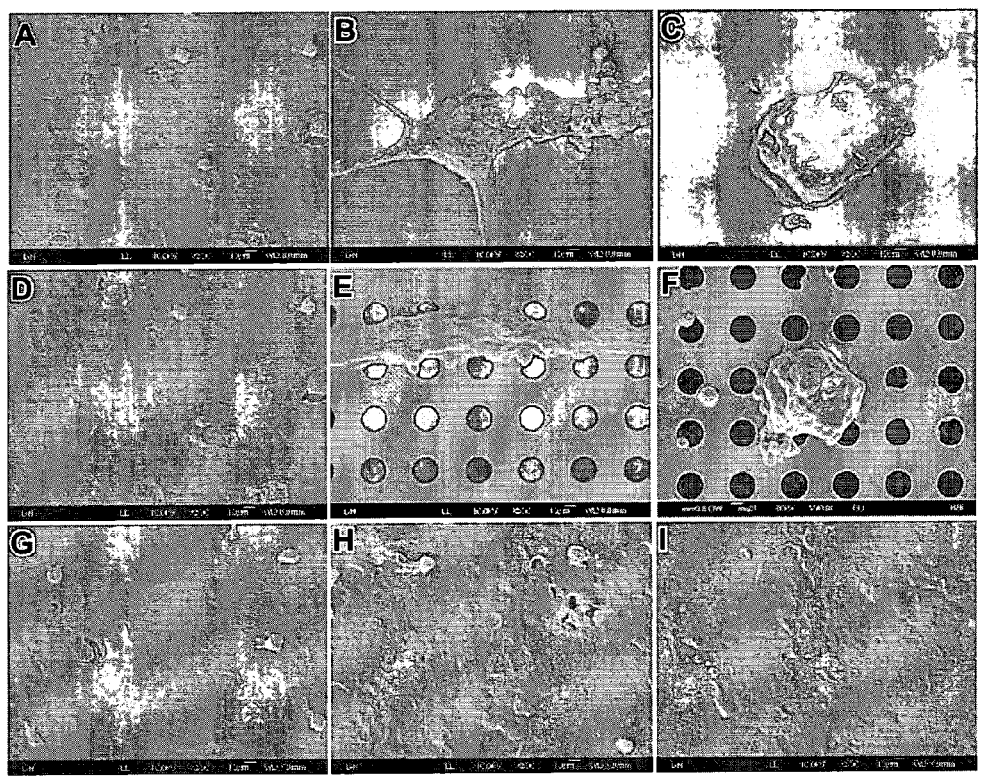
FIG. 2 illustrates by SEM images a test of stability of hepatocyte morphology cultured on galactose-immobilized PET film (A-C), galactose-immobilized $Si_3N_4$ membrane (D-F) and in sandwich configuration, $Si_3N_4$—SC, corresponding to the configuration used in the apparatus of the invention (G-I) throughout 6 days of culture. For the assembly process cf.
Figure 3A:
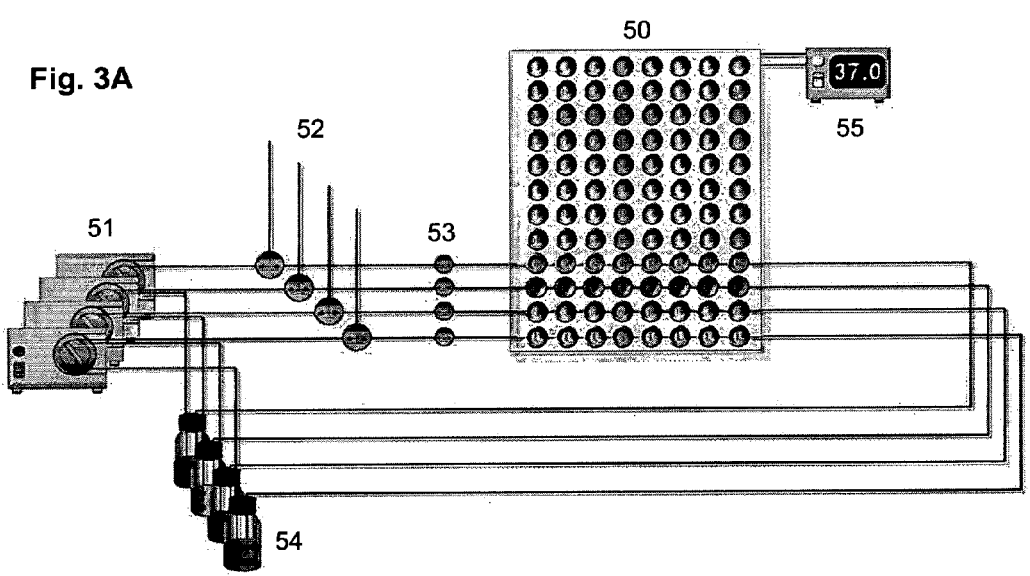
FIG. 3A is a schematic of the perfusion route, 50: 96-well bioreactor, 51: peristaltic pump, 52: three-direction valve, 53: stopping valve, 54: medium reservoir, 55: heating plate.
Figure 4:
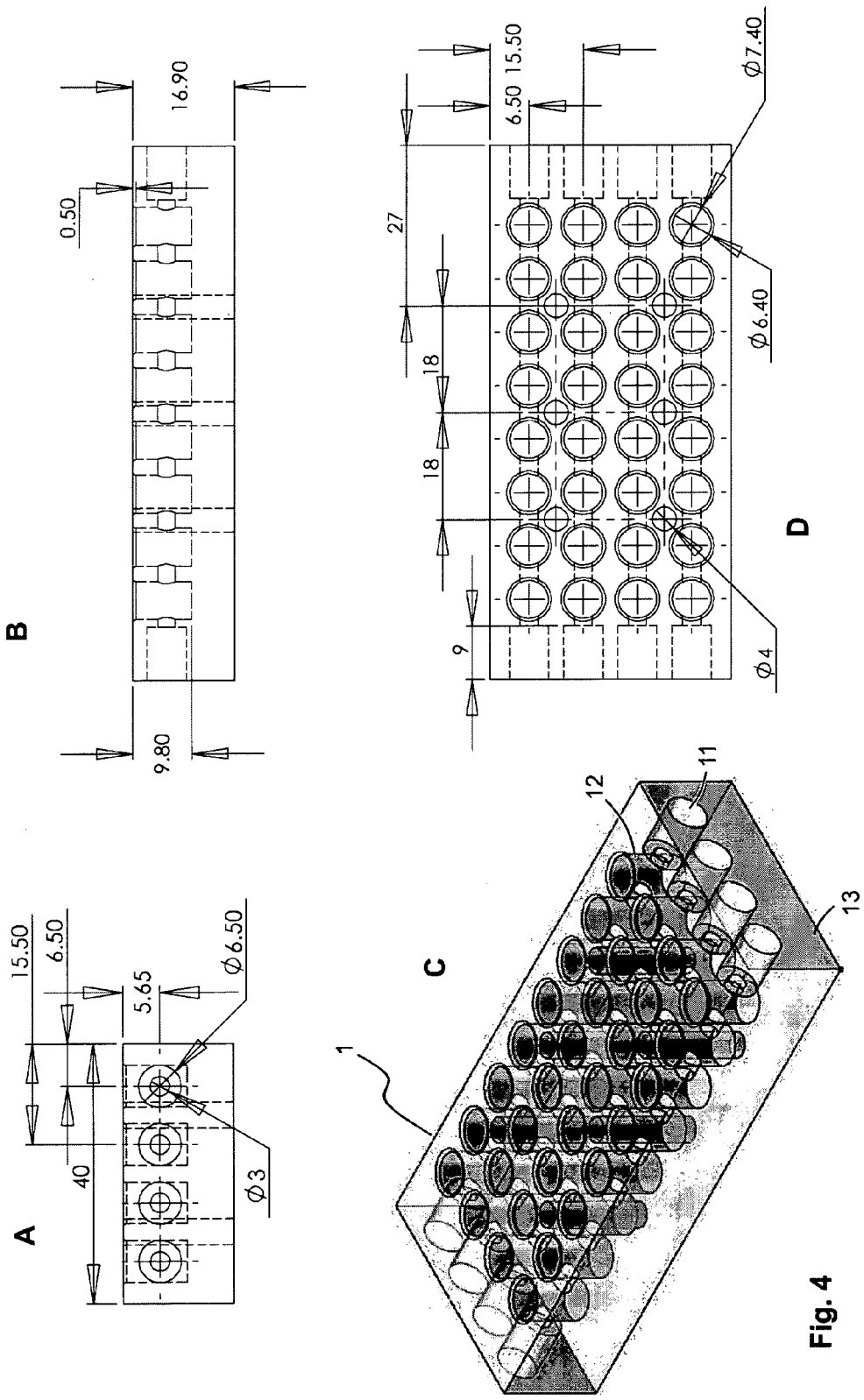
FIG. 4 depicts an exemplary base plate (1) in cross-sectional view seen from the ports of the plate (A), in cross-sectional view seen sidewise along a straight line of recesses (B), in perspective view (C) (11: port, 12: recess of base plate, 13: circumferential wall of base plate) and in top view (D).
Figure 5:
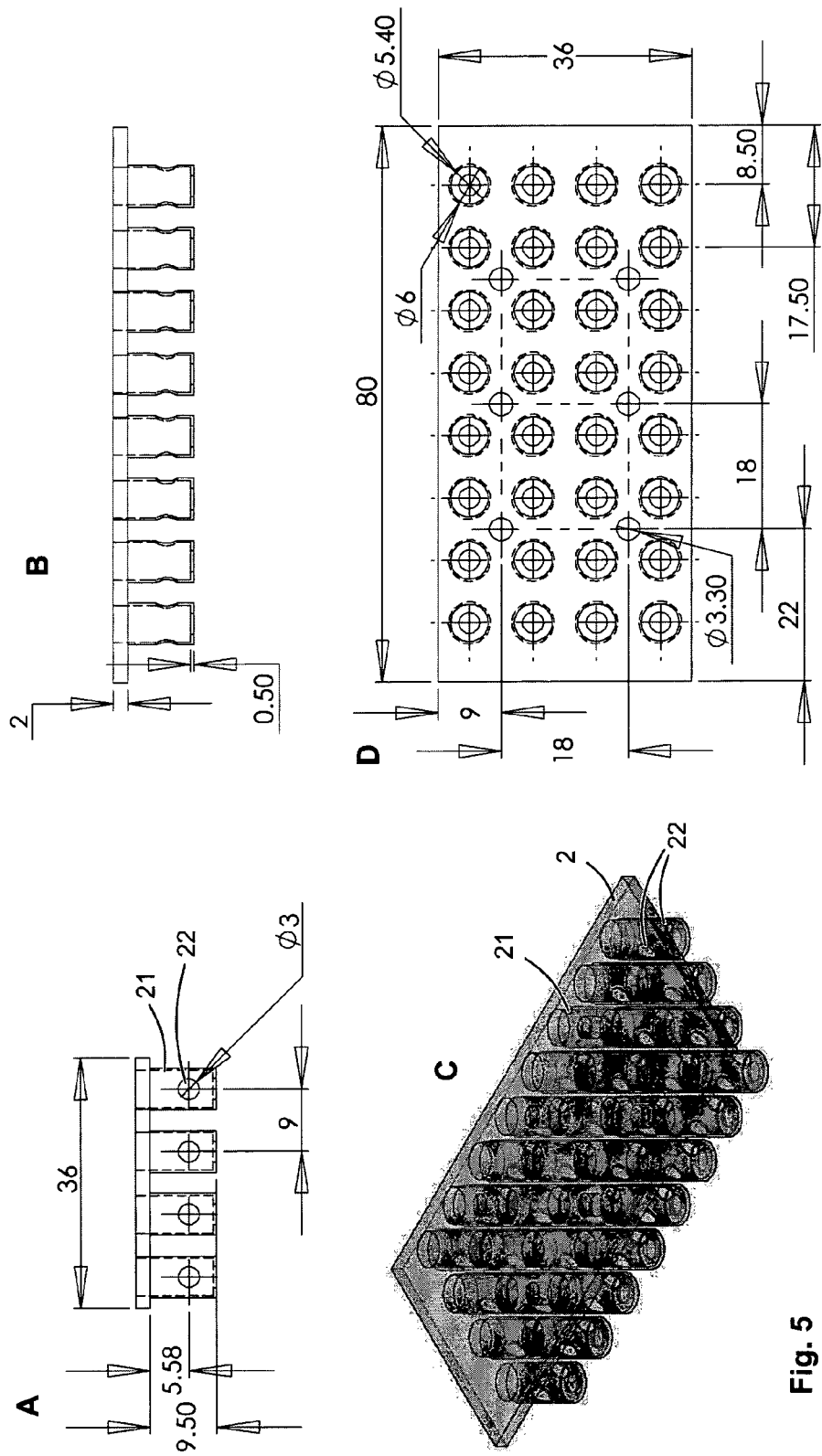
FIG. 5 depicts an exemplary intermediate face (2) in cross-sectional view seen in the direction of a straight line of recesses (A), in cross-sectional view seen sidewise along a straight line of recesses (B), in perspective view (C) (21: recess of intermediate face, 22: opening of recess of intermediate face) and in top view (D).

Primary rat hepatocytes were seeded on galactose-immobilized PET film and overlaid with galactose-immobilized porous $Si_3N_4$ membrane after 24 hrs' culture (FIG. 1) (Zhang, S,. Xia, L, et al., Biomaterials (2008) 29, 29, 3993-4002). Compared with those cultured on galactose-immobilized substrates (FIG. 2A-FIG. 2C and FIG. 2D-FIG. 2F), hepatocytes cultured in the current sandwich configuration maintained a more stable morphology throughout the 6 days of culture (FIG. 2G-FIG. 2I). Stable cell morphology allows a more accurate and consistent analysis of cell functions and drug testing to be carried out at different culture time points Design and Fabrication of 96-Well Bioreactor Device The 96-well bioreactor device was modeled using Solid-Work and had three compartments: the bottom perfusion bioreactor for perfusion route connection, the sieve plate for cell culture and the upper lock plate for sealing the entire assembly (FIG. 4-FIG. 6). A piece of oxygen permeable membrane was placed between the sieve plate and the upper lock plate to allow adequate oxygen to reach the hepatocytes in each well. The wells in bottom perfusion bioreactor as well as the sieve plate were connected by a 3 mm diameter hole, which acts as a medium perfusion channel. The culture medium can be perfused to each well either in series or parallel from the medium reservoir through the pumping action of the peristaltic pumps (FIG. 3).

Flow and Oxygen Profiles in the Bioreactor Under Difference Flow Rates

Figure 8:
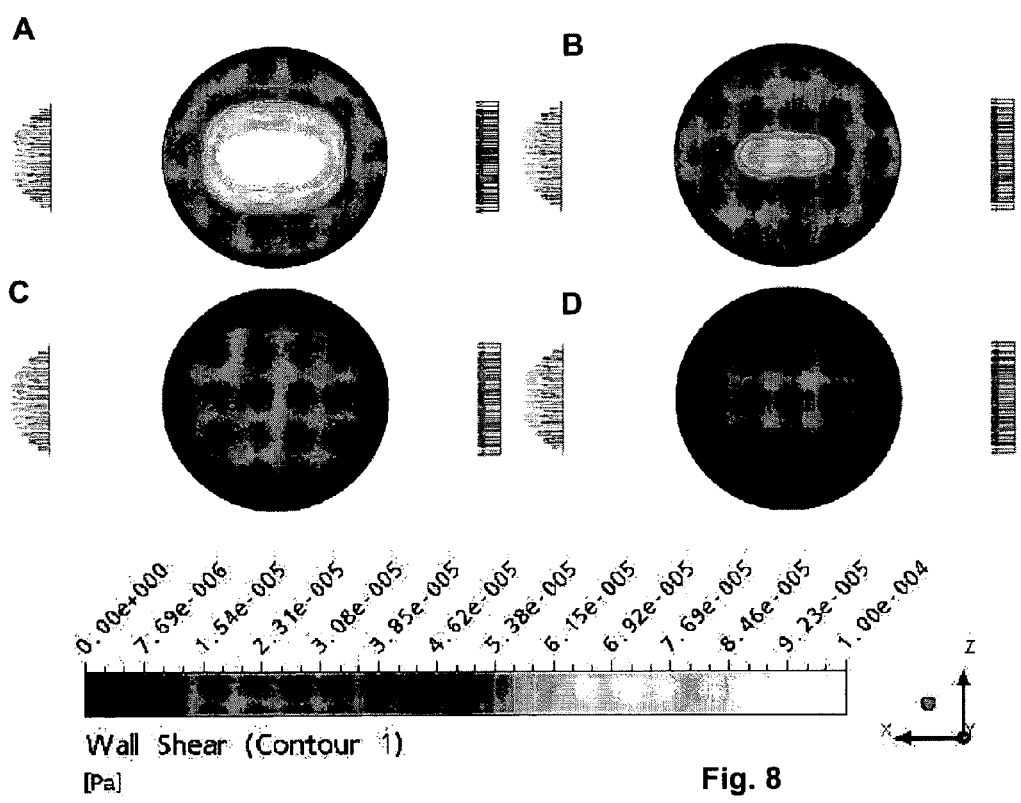
FIG. 8 depicts the wall shear distribution within a 96-well apparatus of the invention at flow rates of 0.1 (A), 0.06 (B), 0.03 (C) and 0.015 ml/min (D).

To select the optimal flow rates for perfusion run in the 96-well bioreactor, we simulated the flow profiles (velocity and wall shear distributions) within the bioreactor at different flow rates of 0.1, 0.06, 0.03 and 0.015 ml/min (FIG. 8, FIG. 9). The results of simulation showed that the generated wall shears in all of flow rates were much lower than the critical value (0.033 Pa). Therefore, the generated wall shear values in all of these four tested flow rates were not detrimental to the cell viability.

Optimization of Flow Rates for Perfusion Culture

To further optimize the flow rates in the perfusion culture, the perfusion was carried out at different flow rates (0.015, 0.03, 0.06, 0.1 ml/min) for up to 6 days, and the cell viability was investigated at the end of perfusion. The process of live and dead staining was described briefly: cells were washed with PBS solution and incubated with Calcein AM (Molecular Probes, USA) and PI at 37° C. for 30 mins according to the standard protocol provided by the suppliers. Then cells were washed with PBS solution and mounted with mounting medium (Dako, Denmark) for confocal viewing. With the exception of cell culture perfused at the flow rate of 0.1 ml/min, cell cultures perfused at other flow rates were still viable after 6 days of perfusion (FIG. 10).

Cell Functions of Rat Hepatocytes in 96-Well Biorector

Liver-specific functions from cultures at flow rates of 0.015, 0.03 and 0.06 ml/min were compared in order to screen for the optimal flow rate for the perfusion cultures. FIG. 11 shows the urea production of hepatocytes cultured in the 96-well bioreactor under different flow rates. The collagen sandwich (sc-s) and $Si_3N_4$—SC (sg-s) under static condition were used as the controls. The results showed that the urea production under perfusion was much higher than those cultured under static condition. The current study showed that the level of urea production observed in hepatocytes culture perfused at flow rate of 0.015 ml/min was consistently higher than those at other flow rates when culture over a period of 6 days.

Long-Term Functional Maintenance of Hapatocytes in Optimized Perfusion Culture

Figure 12:
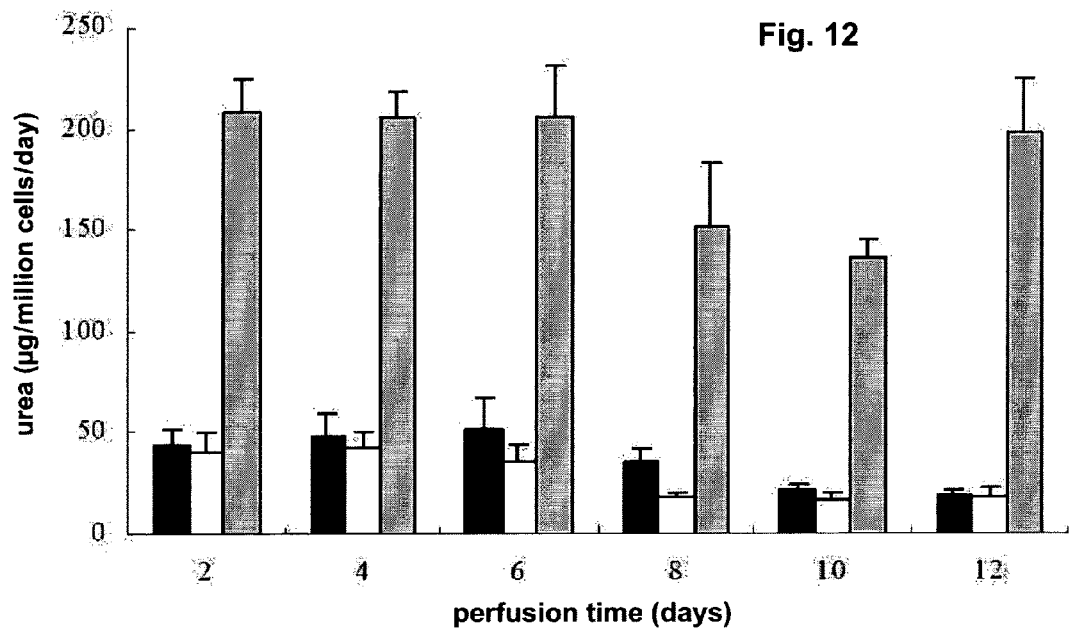
FIG. 12 depicts the urea production of primary hepatocytes during a 12-day culture period in perfusion culture using a static collagen gel sandwich (■), static $Si_3N_4$—SC (□), and $Si_3N_4$—SC perfusion at flow rate of 0.015 ml/min (▨).
Figure 13:
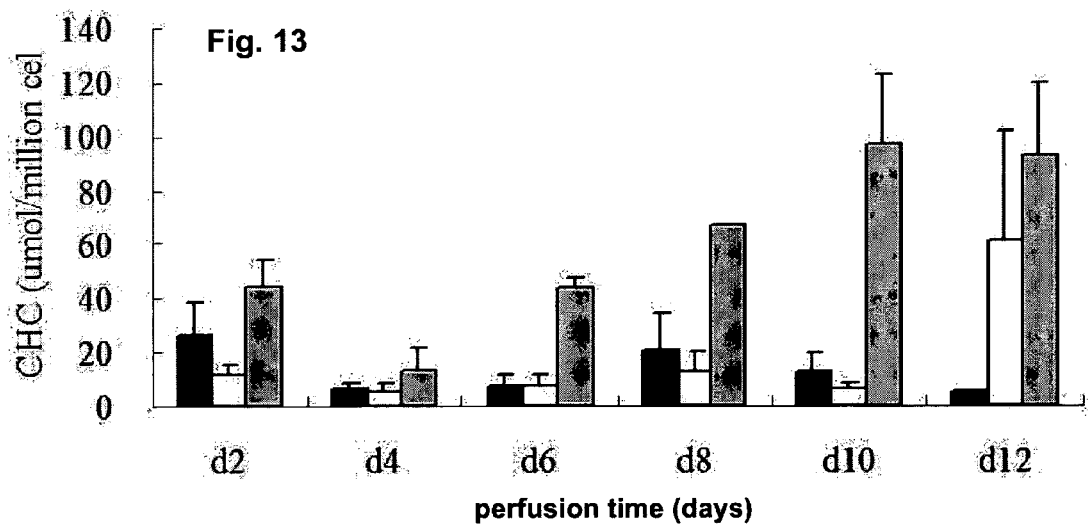
FIG. 13 depicts CYP450 enzymatic activity of primary hepatocytes during a 12-day culture period using a static collagen gel sandwich (■), static $Si_3N_4$—SC (□), and $Si_3N_4$—SC perfusion at flow rate of 0.015 ml/min (▨).

Results from optimization experiments shown that the level of urea production observed in hepatocytes culture perfused at flow rate of 0.015 ml/min was consistently higher than those at other flow rates when cultured over a period of 6 days, so further experiments were done in perfusion at flow rate of 0.015 ml/min. The culture period was extended to 12 days and investigated the liver-specific functions, including urea production and CYP450 (phase I) enzymatic activity by using static collagen gel sandwich and static $Si_3N_4$—SC as controls. The urea production by primary hepatocytes in $Si_3N_4$—SC perfusion is ~200 gg/million cells/day from d2 to d6 and there is a decrease of urea production at d8 and d10, but it recovers to ~200 µg/million cells/day again at d12 (FIG. 12). While the urea produced by hepatocytes in static collagen gel sandwich and static $Si_3N_4$—SC are less than 50 gg/million cells/day during the whole culture period, much lower than that of hepatocytes in $Si_3N_4$—SC perfusion. CYP450 enzymatic activity was measured via highly fluorescent 3-cyano-7-hydroxycoumarin (CHC) production upon incubation with metabolic substrate 3-cyano-7-ethoxycoumarin (CEC) (Molecular Probes, Oreg., USA) by de-alkylation of CEC. The CHC production of hepatocytes in $Si_3N_4$—SC perfusion is ~40 µmol/million cells and decreases to ~15 µmol/million cells, but recovers to ~40 µmol/million cells. There was a significant increase of CHC production at d8 and it was maintained at level of ~100 µmol/million cells at later perfusion culture stage (FIG. 13). While CHC production from the control groups is at the level of less than ~20 µmol/million cells. It indicates that liver-specific functions, especially CYP1A1 and CYP1A2 enzymatic activities, were maintained at the higher level in $Si_3N_4$—SC perfusion.

Uniformity of Cells Cultured Across Different Wells in 96-Well Bioreactor

The uniformity of cells cultured in different wells in the bioreactor was investigated. Since the wells are connected in series, it was analysed whether the cells cultured in different wells demonstrate any gradient effect in nutrient mass transfer and survivability.

Figure 14A:
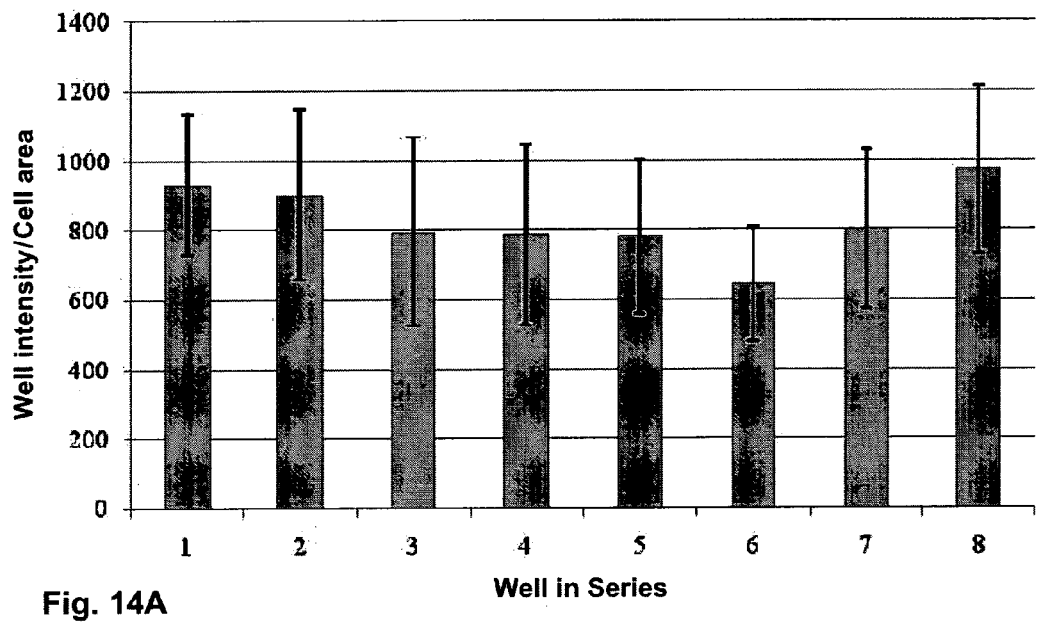
FIG. 14 depicts uniformity of cells cultured across different wells in a 96-well apparatus of the invention in terms of mass transfer efficiency (A) and cell viability (B).
Figure 14B:
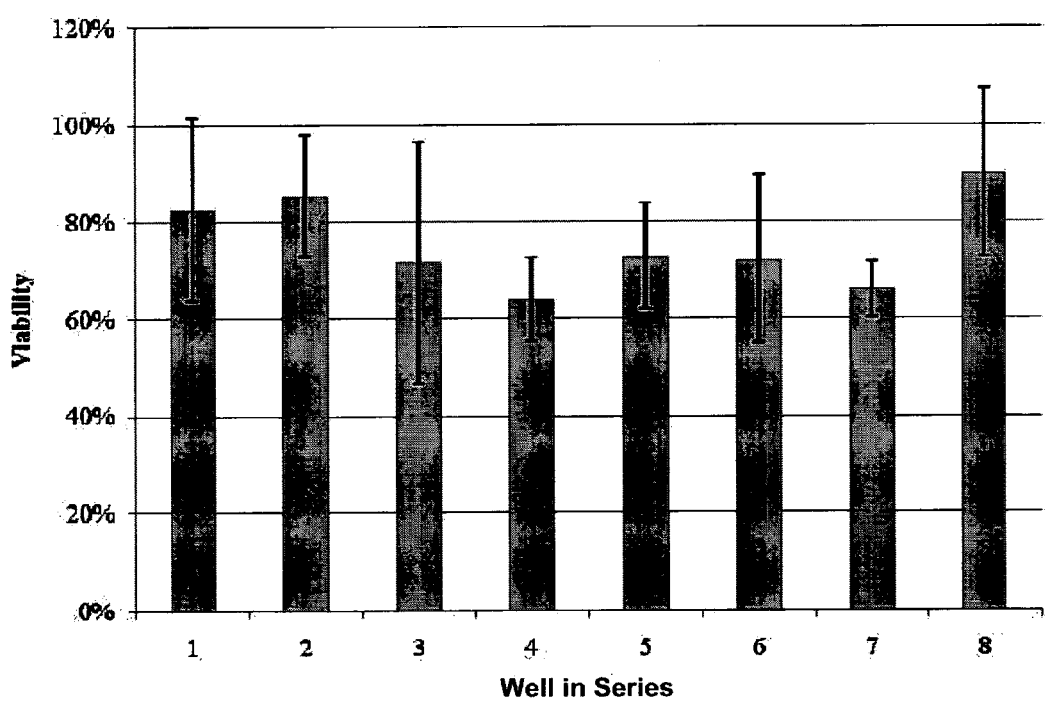

Mass transfer efficiency in different wells in series was investigated by perfusing fluorescence probes in the media (FIG. 14A). The mass transfer efficiency is indicated by fluorescence intensity per cell area. The data show that there is no significant difference between each well in terms of mass transfer efficiency. Accordingly, the mass transfer efficiency, as determined by the fluorescence intensity of the cells labeled by fluorescence probes perfused in the culture, is similar throughout different wells. Cell viability of the cells cultured in different wells in series was investigated by running MTS assay on cells after 2 days of perfusion culture (FIG. 14B). The data show that there is no significant difference between each well in terms of cells viability. Cell viability was therefore comparable in different wells. This shows that the bioreactor is uniform. For a variety of applications such as drug testing purposes, the uniformity of the cells allow for comparisons of results between different wells.

To examine the uniformity of the mass transfer in different wells connected in series, all cells cultured in the bioreactor were first labelled with 20 µM CellTracker Orange (Invitrogen) (red channel). The cells were then transferred to the bioreactor and perfuse-cultured with media containing 3 µM CellTracker Green (Invitrogen) (green channel). After 3 hours, the cells from different wells were fixed and Z-stack images were taken with Olympus FV300 confocal micoscrope. Image processing was then conducted to quantify the mass transfer efficiency. To identify positive areas occupied by cells in each image, red channels were extracted into a separate folder and noise was removed using a low pass filter. Subsequently a mask was created from each image by a thresholding algorithm. The total area for one z-stack image was defined to be the sum of all positive areas in the mask images. Nutrients mass transfer is indicated by the amount of CellTracker Green found on the cells, which is corresponding to the total intensity of the green channel. Total intensity was defined to be the sum of all pixel intensities in the positive areas of the original images. The mass transfer efficiency in each well is then defined as (Total Green Channel Intensity/Total Red Channel Area).

To examine the cell viability uniformity in the different wells, the cells were cultured in the bioreactor for 2 days. After that, they were removed from the biroeactor and transferred to a standard 96-well plate. The cell viability for each well was then measured by MTS assay using the CellTilter 96 Aqueous One Solution Reagent (Promega,USA).

Drug-Induced Hepatotoxicity Tests

Figure 15:
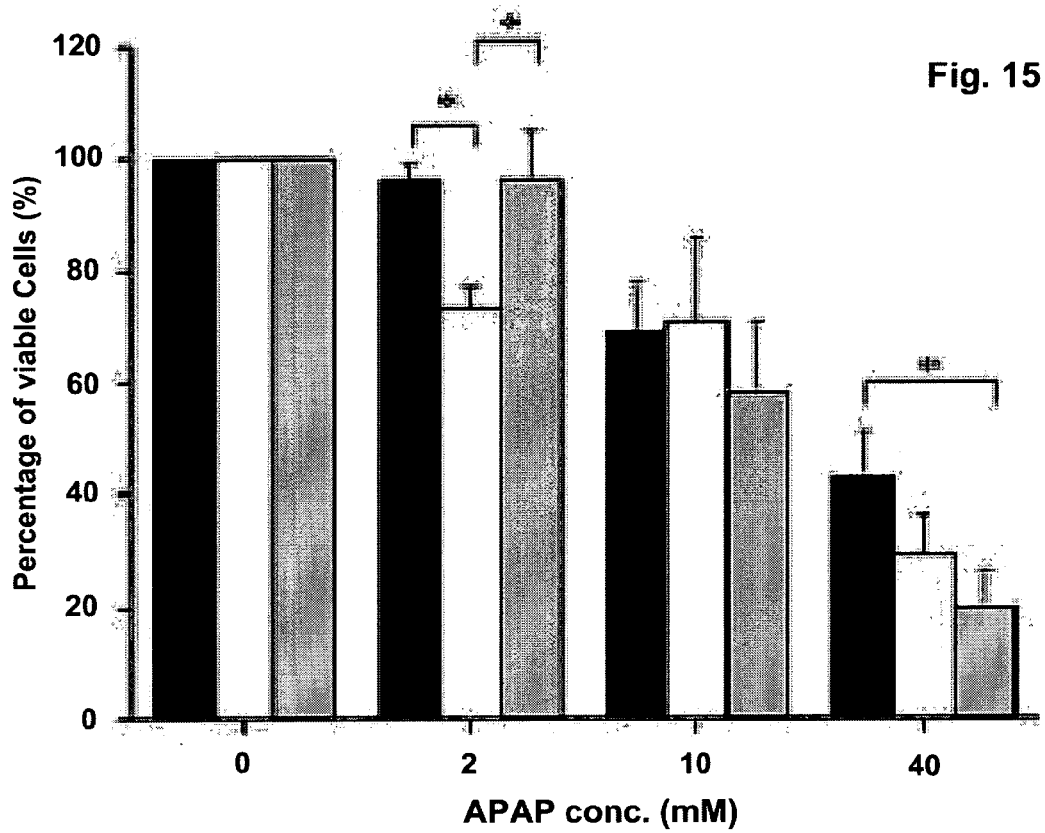
FIG. 15 illustrates a higher drug sensitivity of primary rat hepatocytes in $Si_3N_4$—SCP exposed to APAP. (■: collagen gel sandwich in static condition, □: $Si_3N_4$—SC in static condition, ▨: $Si_3N_4$—SC Perfusion).

Drug-induced hepatotoxicity testing using was conducted using primary rat hepatocytes cultured in the apparatus of the invention in $Si_3N_4$—SCP exposed to APAP. $Si_3N_4$—SC perfusion was observed to show higher sensitivity towards drug-induced hepatotoxicity (FIG. 15).

Hepatocytes cultured in the $Si_3N_4$—SCP were treated with acetaminophen (APAP) (Sigma) to assess their differential responses to drug-induced hepatotoxicity and hepatocytes cultured in static collagen gel sandwich or static $Si_3N_4$—SCP were used as the controls. Hepatocytes in the $Si_3N_4$—SCP and two static sandwich configurations were exposed to drugs for 48 hrs and the cell viability was measured by MTS assay using the CellTilter 96 Aqueous One Solution Reagens (Promega, USA).

$IC_{50}$ Value Measurement in Robotic Liquid Handler

Figure 16:
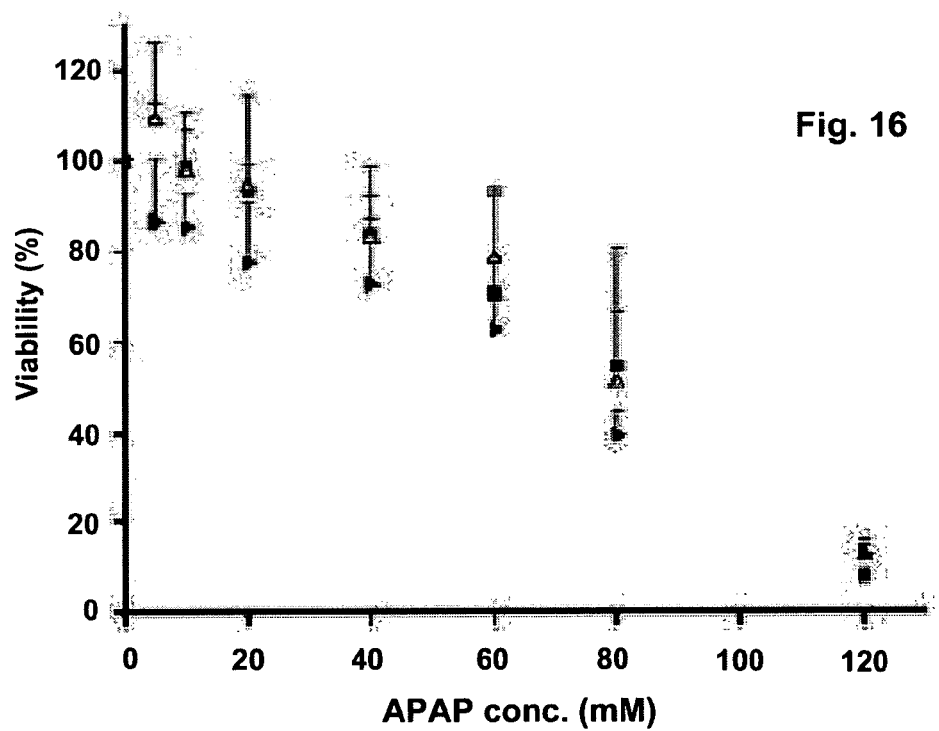
FIG. 16 shows a lower $IC_{50}$ value in $Si_3N_4$—SCP response to APAP-induced hepatotoxicity measured by a robotic liquid handling system. APAP-induced hepatotoxicity was determined in C3A cells ($IC_{50}$ value: 71 mM for $Si_3N_4$—SCP (▨), 80 mM for $Si_3N_4$—SC (■) and 84.6 mM for collagen gel sandwich (□)).

Using the human liver cancer cell line C3A, cultured in the bioreactor, $IC_{50}$ value measurements were conducted with a robotic liquid handler (FIG. 16). The result shows a lower $IC_{50}$ value in $Si_3N_4$—SC perfusion in response to APAP-induced hepatotoxicity. More significantly, this set of result demonstrates that the bioreactor design according to the present invention is compatible with the use of a standard robotic liquid handler that is frequently employed in high throughput screening for candidate compounds with desired pharmaceutical activity. It also demonstrates that other cell types such as human liver cell lines can be cultured in a bioreactor according to the invention.

RESULTS

Wall Shear Stress

Figure 7:
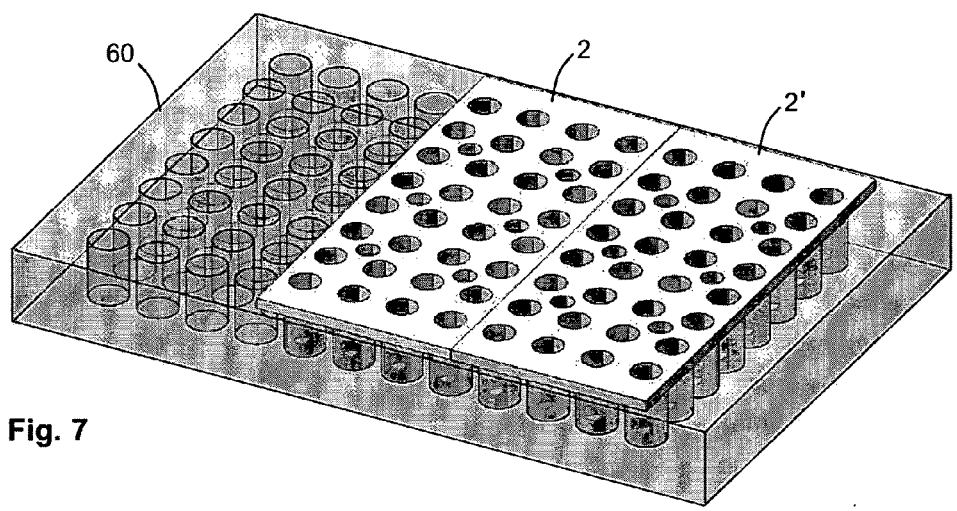
FIG. 7 depicts schematically two intermediated faces (2, 2') of an apparatus of the invention positioned on a conventional multi-well plate (60).

FIG. 11 tabulates the average and maximum wall shear stresses level on the surface of hepatocytes cultures (both top and bottom surfaces of the model). Taking the critical threshold of 0.033 Pa allowable for the hepatocytes culture (Park, J, et al., *Biotechnol Bioeng* (2008) 99, 2, 55-67), the wall shear stress levels generated by both flow rates of 1 and 5 mL/min fall within the acceptable range. On the other hand, the maximum shear stress level generated on the cell surfaces by flow rate of 10 mL/min may be detrimental to the hepatocytes culture. FIG. 7 shows the contour plot of wall shear stress across the surface of the flow between two culture plates at 1 mL/min. Elevated wall shear stresses of approximately 0.0048 Pa were observed at both the inlet and outlet regions of the flow model as the fluid enter and exit the flow volume, respectively. The wall shear level decreased to approximately 0.0016 Pa as the fluid flow between the two plates.

Hepatocyte Viability and Functions

In this study the stack-plate apparatus of the invention was evaluated by culturing rat hepatocytes over a perfusion period of 10 days at 2.12 mL/min, corresponding to a wall shear stress of 0.0042 Pa. This shear stress level has been shown to be well below the critical threshold detrimental to the long-term maintenance hepatocytes culture (Park, et al., 2008, supra). The inlet oxygen partial pressure in the bioreactor was kept at an elevated level of ~466 mmHg, taking into account the serial flow configuration of the bioreactor and the high oxygen consumption rate of the hepatocytes (Park, et al., 2008, supra; Curcio E, et al., *Biomaterials* (2007) 36, 5487-5497; Allen, J W, et al., *Toxicol Sci* (2005) 84, 1, 110-119). FIG. 9 shows the morphology of the 2D monolayer hepatocytes after 24 hours of pre-perfusion static stabilization, before the overlay of the collagen top layer.

The live and dead staining of the hepatocytes after 10 days of perfusion is shown in FIG. 10. Live cells were stained by calcein AM and shown in bright tone (green), while the nuclear of dead cells is stained by PI and shown in red: static culture (A), the bottom layer in perfusion culture (B), the middle layer in perfusion culture (C) and the top layer in perfusion culture (D). As good as all of the hepatocytes in the three different locations within the bioreactor were viable after the 10 days of perfusion. FIG. 14 shows the mitochondrial dehydrogenase activity (%) of the hepatocytes as monitored by the MTS assay after 10 days of perfusion. The activity of the sandwich perfusion culture in the bioreactor was normalized to that of the static cultures. MTS assay was commonly used as an indicator for cell viability. The perfusion culture showed the viability of 194% as compared to that of the static culture at 100%. These results demonstrated that the perfusion hepatocytes culture within a system according to the invention as the bioreactor was able to maintain high viability comparable to those in the static culture. FIG. 15 shows the dehydrogenase activity (%) of individual sandwich culture in the bioreactor after 10 days of perfusion. It can be seen that each perfusion culture plate had viability higher than that observed in the static culture.

In the current study, urea synthesis was used as a representative differentiated function of the hepatocytes in the perfusion culture. FIG. 16 compares the daily urea synthesis rate of both the perfusion and the static cultures. The normalized urea synthesis rates of the perfusion culture were shown to be consistently higher than those in the static culture. A marked decline in the urea synthesis from 73 to 31 $\mu g/\times 10^6$ cells/day was observed in the first two days of the perfusion culture, followed by a gradual decreased from the second to the fourth day, and finally stabilized at a range of 10-20 $\mu g/\times 10^6$ cells/day from the fifth day to the tenth day. For static culture, the urea synthesis rate was below 5 $\mu g/\times 10^6$ cells/day after the fifth day.

Conclusions

A unique perfusion bioreactor system that integrates a surface modified and micro-fabricated sandwich culture technology with a novel 96-well perfusion device is disclosed, which is well suited for use in drug testing applications. The above data demonstrate that the sandwich perfusion system provides an in vivo-like environment for the culturing of primary hepatocyte or other epithelial cells for enhanced and long-term maintenance of cells functions and viability.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments and are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those .skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An apparatus for cell or tissue culture, the apparatus comprising a base plate, an intermediate face and atop plate, the intermediate face being removably sandwiched between the base plate and the top plate,
   wherein the base plate has a circumferential wall a base and a top wall,
   wherein the top wall of the base plate comprises a plurality of recesses arranged in n lines, wherein n is an integer from 1 to about 25 and wherein each line of recesses ranges from a first recess to a last recess, each recess having a circumferential recess wall, wherein the circumferential recess wall of each recess has one recess inlet and one recess outlet,
   wherein the circumferential wall of the base plate comprises a number of 2 n ports, each port being coupled to a single line of recesses of said n lines,
   wherein the recesses of each line of recesses are in fluid communication with (i) each other via the recess inlets and the recess outlets and (ii) with a first and a second port of said 2 n ports, such that the first recess of each line of recesses is coupled to a first port and the last recess of each line of recesses is coupled to a second port,
   wherein the intermediate face has a plurality of recesses arranged in m lines fitted into the plurality of recesses of the top wall of the base plate, wherein m is an integer from 1 to about 25 equal to or smaller than n, and wherein the recesses of the intermediate face have water permeability, and wherein the top plate is reversibly sealed to the intermediate face and the intermediate face is reversibly sealed to the base plate, such that the recesses of the top wall of the base plate define culture chambers, each culture chamber having a circumferential wall defined by the recess wall and a removable top, the top being defined by a portion of the top plate.

2. The apparatus of claim 1, wherein the top plate is of at least essentially water-impermeable material, such that culture chambers defined by the recesses of the top wall of the base plate are in fluid communication with the ambience only via the recess inlet and the recess outlet within the top wall of the base plate.

3. The apparatus of claim 1., wherein the water permeability of the recesses of the intermediate face is provided by an aperture comprised in each recess.

4. The apparatus of claim 1, wherein the recesses of the intermediate face are of gas-permeable material.

5. The apparatus of claim 1, wherein the number of recesses of at least one line of the m lines of recesses of the intermediate face is identical to the number of recesses in at least one line of the n lines of recesses of the top wall of the base plate, such that each culture chamber defined by a recess of the top wall of the base plate has a recess of the intermediate face fitted therein.

6. The apparatus of claim 1, wherein one or more of the recesses of the intermediate face have an outer shape and outer dimensions that correspond to the inner shape and the inner dimensions of the recesses of the top wall of the base plate into which the recesses are fitted.

7. The apparatus of claim 1, wherein the intermediate face has a shape and dimensions that match the shape and dimensions of the top wall of the base plate.

8. The apparatus of claim 1, wherein the intermediate face has a shape and dimensions that match the shape and dimensions of the top wall of the base plate in such a way that the at least one line of recesses of the intermediate fits into the at least one line of recesses of the top wall of the base plate that has an identical number of recesses.

9. The apparatus of claim 1, wherein the top plate has one or more recesses, the recesses of the top plate being arranged at positions of recesses of the intermediate face, such that one or more culture chambers defined by the recesses of the top wall of the base plate have a circumferential wall defined by the recess wall and a removable top, the top being defined by a portion of the top plate that comprises the recesses thereof.

10. The apparatus of claim 1, wherein the top plate has a shape and dimensions that match the shape and dimensions of the intermediate face.

11. The apparatus of claim 1, wherein each line of recesses in the top wall of the base plate has an independently selected number of o recesses, wherein o is an integer from 1 to about 100.

12. The apparatus of claim 1, wherein the integers o of all lines of recesses in the top wall of the base plate are identical.

13. The apparatus of claim 1, wherein each line of recesses in the intermediate face has an independently selected number of p recesses, wherein p is an integer from 1 to about 100.

14. The apparatus of claim 1, wherein the number p of recess of each line of recesses in the intermediate face is identical to the number o of recesses in the top wall of the base plate into which the line of recesses in the intermediate face is fitted.

15. The apparatus of claim 1, wherein the numbers p of all lines of recesses in the intermediate face are identical.

\* \* \* \* \*